(12) United States Patent
Wilson et al.

(10) Patent No.: US 11,493,494 B2
(45) Date of Patent: Nov. 8, 2022

(54) DETECTION SYSTEM

(71) Applicant: USA SANDS, LLC, Sandy Springs, GA (US)

(72) Inventors: Richard D. Wilson, Orinda, CA (US); Axel James Perez, Jacksonville, FL (US); Dennis Duke, St. Augustine, FL (US)

(73) Assignee: USA SANDS, LLC, Sandy Springs, GA (US)

( * ) Notice: Subject to any disclaimer, the term of this patent is extended or adjusted under 35 U.S.C. 154(b) by 365 days.

(21) Appl. No.: 16/697,645

(22) Filed: Nov. 27, 2019

(65) Prior Publication Data

US 2020/0173970 A1    Jun. 4, 2020

Related U.S. Application Data

(60) Provisional application No. 62/772,864, filed on Nov. 29, 2018.

(51) Int. Cl.
| | | |
|---|---|---|
| *G01N 33/00* | (2006.01) | |
| *G01N 21/31* | (2006.01) | |
| *G01N 15/14* | (2006.01) | |

(52) U.S. Cl.
CPC ......... *G01N 33/0057* (2013.01); *G01N 15/14* (2013.01); *G01N 21/31* (2013.01); *G01N 2015/1486* (2013.01)

(58) Field of Classification Search
CPC ........... G01N 15/14; G01N 2015/1486; G01N 21/31; G01N 33/0057; G01N 24/00

USPC ......................................................... 73/23.2
See application file for complete search history.

(56) References Cited

U.S. PATENT DOCUMENTS

| | | |
|---|---|---|
| 645,576 A | 3/1900 | Tesla |
| 8,242,447 B1 | 8/2012 | Chawla |
| 2008/0156997 A1 | 7/2008 | Kearfott |
| 2011/0050241 A1 | 3/2011 | Nutting et al. |
| 2011/0233419 A1 | 9/2011 | Norris |
| 2017/0350834 A1 | 12/2017 | Prado et al. |

OTHER PUBLICATIONS

Kumar et al., Wireless Power Transmission: A Review; Global Journal of Engineering Science and Researches Conference, Dec. 2016, pp. 119-122.
Singh et al.; Wireless Transmission of Electrical Power Overview of Recent Research & Development; International Journal of Computer and Electrical Engineering, Apr. 2, 2012 vol. 4, No. 2, pp. 207-211.
Vinge, R.; Wireless Energy Transfer by Resonant Inductive Coupling: Master of Science Thesis; Department of Signals and systems, Chalmers University of Technology, Göteborg, Sweden, 2015.
Van Roy, Introduction to RT1650 Wireless Power Receiver; Sep. 2015, AN036 pp. 1-15.
Search Report for International Application No. PCT/US2019/063568; dated Mar. 19, 2020.

*Primary Examiner* — Tri T Ton
(74) *Attorney, Agent, or Firm* — Barnes & Thornburg LLP; Jason A. Bernstein

(57) ABSTRACT

System and method for detecting the presence at a distance of materials utilizing the atomic structure and characteristics of the elements in the chemicals comprising the material.

21 Claims, 22 Drawing Sheets

| SYM-BOL | NAME | P.E. | N. | MASS (150) | ATOMIC WEIGHT | TOT. NO. |
|---|---|---|---|---|---|---|
| H | Hydrogen | 1 | | 1 | 1.00797 | 2 |
| He | Helium | 2 | 2 | 4 | 4.0026 | 6 |
| Li | Lithium | 3 | 4 | 7 | 6.939 | 10 |
| Be | Beryllium | 4 | 5 | 9 | 9.0122 | 13 |
| B | Boron | 5 | 6 | 11 | 10.811 | 16 |
| C | Carbon | 6 | 6 | 12 | 12.01115 | 18 |
| N | Nitrogen | 7 | 7 | 14 | 14.0067 | 21 |
| O | Oxygen | 8 | 8 | 16 | 15.9994 | 24 |
| F | Fluorine | 9 | 10 | 19 | 18.9934 | 28 |
| Ne | Neon | 10 | 10 | 20 | 20.183 | 30 |
| Na | Sodium | 11 | 12 | 23 | 22.9898 | 34 |
| Mg | Magnesium | 12 | 12 | 24 | 24.313 | 36 |
| Al | Aluminum | 13 | 14 | 27 | 26.9815 | 40 |
| Si | Silicon | 14 | 14 | 28 | 28.086 | 42 |
| P | Phosphorus | 15 | 16 | 31 | 30.9738 | 46 |
| S | Sulfur | 16 | 16 | 32 | 32.064 | 48 |
| Cl | Chlorine | 17 | 18 | 35 | 35.453 | 52 |
| Ar | Argon | 18 | 22 | 40 | 39.948 | 58 |
| K | Potassium | 19 | 20 | 39 | 39.101 | 58 |
| Ca | Calcium | 20 | 20 | 40 | 40.08 | 60 |
| Sc | Scandium | 21 | 24 | 45 | 44.956 | 66 |
| Ti | Titanium | 22 | 26 | 48 | 47.90 | 70 |
| V | Vanadium | 23 | 28 | 51 | 50.942 | 74 |
| Cr | Chromium | 24 | 28 | 52 | 51.996 | 76 |
| Mn | Manganese | 25 | 30 | 55 | 54.938 | 80 |
| Fe | Iron | 26 | 30 | 56 | 55.847 | 82 |
| Co | Cobalt | 27 | 32 | 59 | 58.9332 | 86 |
| Ni | Nickel | 28 | 30 | 58 | 58.71 | 86 |
| Cu | Copper | 29 | 34 | 63 | 63.54 | 92 |
| Zn | Zinc | 30 | 34 | 64 | 55.37 | 94 |
| W | Gallium | 31 | 38 | 69 | 69.72 | 100 |
| Ge | Germanium | 32 | 42 | 74 | 72.59 | 106 |
| As | Arsenic | 33 | 42 | 75 | 74.9216 | 108 |
| Se | Selenium | 34 | 46 | 80 | 78.96 | 114 |
| Br | Bromine | 35 | 44 | 79 | 79.909 | 114 |
| Kr | Krypton | 36 | 48 | 84 | 83.80 | 120 |
| Rb | Rubidium | 37 | 48 | 85 | 85.47 | 122 |
| Sr | Strontium | 38 | 50 | 88 | 87.62 | 126 |
| Y | Yttrium | 39 | 50 | 89 | 88.905 | 128 |
| Zr | Zirconium | 40 | 50 | 90 | 91.22 | 130 |

FIG. 9Ai

| SYM-BOL | NAME | P.E. | N. | MASS (150) | ATOMIC WEIGHT | TOT. NO. |
|---|---|---|---|---|---|---|
| Nb | Niobium | 41 | 52 | 93 | 92.906 | 134 |
| Mo | Molybdenum | 42 | 56 | 98 | 95.94 | 140 |
| Te | Technetium | 43 | 56 | (99) | 98.906 | 142 |
| Ru | Ruthenium | 44 | 58 | 102 | 101.07 | 145 |
| Rh | Rhodium | 45 | 58 | 103 | 102.905 | 148 |
| Pd | Palladium | 46 | 60 | 106 | 106.4 | 152 |
| Am | Americium | 95 | 148 | (243) | 146 (241) | |
| Ag | Silver | 47 | 50 | 107 | 107.870 | 154 |
| Cd | Cadmium | 48 | 66 | 114 | 112.40 | 162 |
| In | Indium | 49 | 66 | 115 | 114.82 | 164 |
| Sn | Tin | 50 | 70 | 120 | 118.68 | 170 |
| Sb | Antimony | 51 | 70 | 121 | 121.75 | 172 |
| Te | Tellurium | 52 | 78 | 130 | 127.60 | 180 |
| I | Iodine | 53 | 74 | 127 | 126.9004 | 180 |
| Xe | Xenon | 54 | 78 | 132 | 131.30 | 186 |
| Cs | Cesium | 55 | 78 | 133 | 132.905 | 188 |
| Ba | Barium | 56 | 82 | 138 | 137.34 | 194 |
| La | Lanthanum | 57 | 82 | 199 | 138.91 | 196 |
| Ce | Cerium | 58 | 82 | 140 | 140.12 | 198 |
| Pr | Praseodymium | 59 | 82 | 141 | 140.97 | 200 |
| Nd | Neodymium | 60 | 82 | 142 | 144.24 | 202 |
| Pm | Promethium | 61 | 84 | (145) | 144.91 | 206 |
| Sm | Samarium | 62 | 90 | 152 | 150.35 | 214 |
| Eu | Europium | 63 | 90 | 153 | 131.98 | 216 |
| Gd | Gadolinium | 64 | 94 | 158 | 157.25 | 222 |
| Tb | Terbium | 85 | 94 | 159 | 158.924 | 224 |
| Dy | Dysprosium | 66 | 98 | 164 | 162.50 | 230 |
| Ho | Holmium | 67 | 98 | 165 | 164.930 | 232 |
| Er | Erbium | 68 | 98 | 166 | 167.26 | 234 |
| Tm | Thulium | 69 | 100 | 169 | 168.934 | 238 |
| Yb | Ytterbium | 70 | 104 | 174 | 173.04 | 244 |
| Lu | Lutetium | 71 | 104 | 175 | 174.97 | 246 |
| Hf | Hafnium | 72 | 108 | 180 | 178.49 | 252 |
| Ta | Tantalum | 73 | 108 | 182 | 180.948 | 255 |
| W | Tungsten | 74 | 110 | 184 | 183.85 | 258 |
| Re | Rhenium | 75 | 112 | 187 | 186.2 | 262 |
| Os | Osmium | 76 | 116 | 192 | 190.2 | 268 |
| Ir | Iridium | 77 | 116 | 193 | 192.2 | 270 |

FIG. 9Aii

| SYM-BOL | NAME | P.E. | N. | MASS (150) | ATOMIC WEIGHT | TOT. NO. |
|---|---|---|---|---|---|---|
| Pt | Platinum | 78 | 117 | 195 | 195.09 | 273 |
| Au | Gold | 79 | 118 | 197 | 196.967 | 276 |
| Hg | Mercury | 80 | 122 | 202 | 200.59 | 282 |
| Tl | Thallium | 81 | 124 | 205 | 204.89 | 286 |
| Pb | Lead | 82 | 126 | 208 | 207.19 | 291 |
| Bi | Bismuth | 83 | 126 | 209 | 208.980 | 292 |
| Po | Polonium | 84 | 126 | (210) | 210.0 | 294 |
| At | Astatine | 85 | 125 | (210) |  | 295 |
| Rn | Radon | 86 | 136 | (222) | 222.0 | 308 |
| Fr | Francium | 87 | 136 | (223) |  | 310 |
| Ra | Radium | 88 | 138 | (226) | 226.05 | 314 |
| Ac | Actinium | 89 | 138 | (227) | 227.0 | 316 |
| Th | Thorium | 90 | 142 | (232) | 282.04 | 322 |
| Pa | Protactinium | 91 | 140 | (281) |  | 322 |
| U | Uranium | 92 | 148 | (298) | 238.03 | 330 |
| Np | Neptunium | 93 | 144 | (237) |  | 330 |
| Pu | Plutonium | 94 | 160 | (244) | 145 (289) | 338 |

FIG. 9Aiii

PARAFFIN OR ALKANE -- $C_nH_{2n+2}$ -- 30% of Crudes

| BASE | FORM-ULA | NAME | N. | M | COMM. NAME | INTER-FERENCE | P | N | M | BASE | FORM-ULA | I.P | P | N | M | M/N |
|---|---|---|---|---|---|---|---|---|---|---|---|---|---|---|---|---|
| 10 | $CH_4$ | Methane | .6 | 16 | | | Na | F | | | | | | | | |
| 18 | $C_2H_6$ | Ethane | 12 | 30 | | . | Ar | Cl | | | | | | | | |
| 26 | $C_3H_8$ | Propane | 18 | 42 | Fuel Gases | | Fe | Ti | | | | | | | | |
| 34 | $C_4H_{10}$ | Butane | .24 | 58 | | | Se | Cu | | NAPTHENE ($CnH2n$) 49% of crudes | | | | | | |
| 42 | $C_5H_{12}$ | Pentane | 30 | 72 | Petroleum Ether Naptha | | Mo | As | | 40 | $C_5H_{10}$ | Ba Li | Zr | | Ar | 30/70 |
| 50 | $C_6H_{14}$ | Hexane | 36 | 86 | | | B Sn | Y-Sr Zr | | 48 | $C_6H_{12}$ | Ba B | Cd | Kr Rd | Ti | 38/84 |
| 58 | $C_7H_{16}$ | Heptane | .42 | 100 | | C | Ce | Ru Rh | Ni | 56 | $C_7H_{14}$ | C B | Ba | Mo Ta | Fe | 42/98 |
| 66 | $C_8H_{18}$ | Octane | .48 | 114 | Gasoline | C | Dy | Cd In | | 64 | $C_8H_{16}$ | C B | Gd | | Zn | 48/112 |
| 74 | $C_9H_{20}$ | Nonane | 54 | 128 | | N | W | I | Ge | 72 | $C_9H_{18}$ | N | Hf | | | 54/126 |
| 82 | $C_{10}H_{22}$ | Decane | .60 | 142 | | | Pb | Ba La Ca Pr Nd | | 80 | $C_{10}H_{20}$ | O | Hg | | Se | 60/140 |
| 90 | $C_{11}H_{24}$ | Undecane | 66 | 158 | | | F Th | Sm Eu | Zr | 88 | $C_{11}H_{22}$ | Fl | Ra | | Sr | 66/154 |
| 98 | $C_{12}H_{26}$ | | 72 | 170 | Kerosine | Meth | | Dy Ho | Mo | 96 | $C_{12}H_{24}$ | Ne | | | | 72/168 |
| 106 | $C_{13}H_{28}$ | | 78 | 184 | | Ag | | | Pd | 104 | $C_{13}H_{26}$ | Ne | Yb Lu | | | 78/182 |
| 114 | $C_{14}H_{30}$ | | 84 | 198 | | C | | | Cd | 112 | $C_{14}H_{28}$ | Na | Re | | | 84/196 |
| 122 | $C_{15}H_{32}$ | Penda-Decane | 90 | 212 | | C | | Hg | | 120 | $C_{15}H_{30}$ | C Mg | Na | --- | Sn | 90/210 |
| 130 | $C_{16}H_{34}$ | Hexa-Decane Cetane | 96 | 226 | | | Al | | Te | 128 | $C_{16}H_{32}$ | Al | | | | 96/224 |
| 138 | $C_{17}H_{36}$ | | 102 | 240 | | Dr-Metd | | | Be | 136 | $C_{17}H_{34}$ | Sl | | Rm | | 102/275 |
| 146 | $C_{18}H_{38}$ | | 108 | 254 | Semisolids, | P Ba. | | U | | 144 | $C_{18}H_{36}$ | Sl | . | U | | 108/252 |
| 154 | $C_{19}H_{40}$ | | 114 | 268 | Petroleum Jellies | P Fla. | | | | 152 | $C_{19}H_{38}$ | P Rs | | | Sm | 114/266 |
| 162 | $C_{20}H_{42}$ | | 120 | 282 | | S | | | | 160 | $C_{20}H_{40}$ | S | | | | 120/280 |
| 170 | $C_{21}H_{44}$ | | 126 | 296 | Lubricating Oil | | Cl | | | $C_{21}H_{42}$ to $C_{31}H_{62}$ Base Numbers | | | | | | |

FIG. 9B1

PARAFFIN OR ALKANE – $C_nH_{2n+2}$ – 30% of Crudes

| BASE | FORM-ULA | NAME | N. | M | COMM. NAME | INTER-FERENCE | P | N | M | BASE | | | | | | |
|---|---|---|---|---|---|---|---|---|---|---|---|---|---|---|---|---|
| 178 | $C_{22}H_{46}$ | | 132 | 310 | | Eth-ane | | | | 168-176-184-192-200-208-216 | | | | | | |
| 186 | $C_{23}H_{48}$ | | 136 | 324 | | Eth-ane | | | | 224-232-240-248 | | | | | | |
| 194 | $C_{24}H_{50}$ | Tetra (Lube Cosone Oil) | 144 | 336 | | | K | | Fl | | | | | | | |
| 202 | $C_{25}H_{52}$ | | 150 | 352 | | | Ca | Ca K | Ne Hg | AROMATIC or BENZENE | | | | | | $C_nH_{2n-2}$ |
| 210 | $C_{26}H_{54}$ | | 156 | 366 | Constitue nts of Paraffin | | | | Po As | 15% of crudes | | | | | | N M |
| 218 | $C_{27}H_{56}$ | | 162 | 380 | | Ti Ar | | | | 42 | $C_6H_6$ | Ba | Mo | As | | 30 78 |
| 226 | $C_{28}H_{58}$ | | 168 | 394 | | Y Na | | | Ra | 50 | $C_7H_8$ | Au Sn | Sn | Y Zr | | 42 92 |
| 234 | $C_{29}H_{60}$ | | 174 | 408 | | Y Na | | | | 58 | $C_8H_{10}$ | C | Ce | Ru Rh | Ni | 48 108 |
| 242 | $C_{30}H_{42}$ | | 180 | 422 | | Cr Hg Fe | | | | 90 | $C_{12}H_{18}$ | Fl | Th | Sm Bu | Zr | 72 162 |
| 250 | $C_{31}H_{64}$ | | 186 | 436 | | Mn | | | | 146 | $C_{19}H_{32}$ | P Fl S | | | | 114 260 |
| | | | | | | | | | | 250 | $C_{32}H_{66}$ | Mn | | | | 192 412 |
| | | | | | | | | | | ASPHALTICS – 6% of CRUDES | | | | | | |
| | | | | | | | | | | 40 to 60 C. Atoms | | | | | | |

FIG. 9Bii

| MORE COMPOUNDS: | P | N | M |
|---|---|---|---|
| Acetone $CH_3COCH_3$ | 32 | 26 | 58 |
| Aspirine $CH_3COOCaH_4COOH$ | 94 | 34 | 128 |
| Formaldihyde HCHO | 16 | 14 | 30 |
| Hydrochloric Acid HCl | 18 | 18 | 36 |
| Calcium Hypochlorite $Ca(OCl)_2$ | 70 | 72 | 142 |
| Sodium Hypochlorite NaOCl $5d_2C$ | 46 | 46 | 92 |
| Sodium Hydroxide (LTE) $Na_2O$ | 30 | 32 | 62 |
| Titanium Dioxide $TiO_2$. | 38 | 42 | 80 |
| Triacetone Triperoxide (TATP) $C_9H_{18}O_6$ | 120 | 102 | 222 |
| Marijuana (SVH) $C_{21}H_{30}O_2$ | 172 | 142 | 314 |

FIG. 9C

| "CLEAN" FREQ. (Sun Declination) |||
| :---: | :---: | :---: | :---: |
| 0° = 64d71×360 = 24,901.5 ÷ 186,282 = 7.481 ||||
| 23°27' s.91741 × 69,171 = 63,458 × 360 = 22,845. ||||
| 186,282 = 8.154 – 7.481 = .673 ÷ 3 = ||||
| .2243 / Mc. ||| .2243 ÷ 30.4 = .0074/Day ||||
| MO. & DAY | SUN MERIDIAN | SUN DECL. | FREQ HTZ. |
| JAN 7 | 12:06 | 22°23' | 8.041 |
| JAN 21 | 12:11 | 19°58' | 7.929 |
| FEB 7 | 12:14 | 15°21' | 7.817 |
| FEB 21 | 12:13 | 10°37' | 7.705 |
| MAR 7 | 12:11 | 5°20' | 7.593 |
| MAR 21 | 12:07 | 0°0' | 7.481 |
| APR 7 | 12:02 | 6°46' | 7.593 |
| APR 21 | 11:58 | 11°48' | 7.705 |
| MAY 7 | 11:58 | 16°46' | 7.817 |
| MAY 21 | 11:58 | 20°09' | 7.429 |
| JUN 7 | 11:59 | 22°42' | 8.041 |
| JUN 21 | 12:02 | 23°26' | 8.153 |
| JUL 7 | 12:05 | 22°38' | 8.041 |
| JUL 21 | 12:08 | 20°80' | 7.929 |
| AUG 7 | 12:06 | 16°28' | 7.817 |
| AUG 22 | 12:03 | 11°50' | 7.705 |
| SEPT 7 | 11:58 | 6°08' | 7.593 |
| SEPT 23 | 11:52 | 0°0' | 7.481 |
| OCT 7 | 11:48 | 5°26' | 7.593 |
| OCT 21 | 11:44 | 10°36' | 7.705 |
| NOV 7 | 11:44 | 15°58' | 7.817 |
| NOV 21 | 11:46 | 19°52' | 7.929 |
| DEC 7 | 11:51 | 22°35' | 8.041 |
| DEC 21 | 11:58 | 23°26' | 8.153 |

FIG. 10

DETECTION SYSTEM

PRIORITY CLAIM

This application claims priority under 35 U.S.C. § 119(e) to U.S. Provisional Application Ser. No. 62/772,864, filed Nov. 29, 2018, the disclosure of which is expressly incorporated by reference herein in its entirety.

FIELD OF THE DISCLOSURE

The present disclosure relates to a detection system, and particularly to a detection system for locating materials. More particularly, the present disclosure relates to an element detection system that can detect materials through the fundamental atomic structure and characteristics of various elements of the Periodic Table and compounds thereof contained in the material to be detected.

BACKGROUND

Various detection systems have been developed for locating materials of interest, such as explosive materials for combatting terrorism. However, existing systems suffer from one or more disadvantageous limitations.

Current methods for detecting and locating target materials focus on radioactive, gaseous, electrical, or similar emissions as well as metallic, magnetic, X-ray, or chromatography to scan subject materials for detecting certain substances by their physical or chemical characteristics. Such detection systems include, but are not limited to, radiation detectors, metal detectors, chemical scanners, chromatographs, X-ray, and similar detection systems. Metal detectors, for example, rely on the magnetic properties of certain metals and a less scientifically understood practice of "dousing".

Personnel screening systems utilized at passenger terminals are known, but rely on detection schemes that are limited to only a few inches or feet, and can be used only for discrete items, for example, weapons and explosives.

In other systems and methods for protecting against terrorism, when a vehicle enters a secure area, such as a military base, they are inspected visually, which can miss dangerous items. The vehicles may also be inspected by a canine unit, if one is available, and many times they are not available. But in such instances, the inspection time must be low enough so as not to hamper traffic flow. In other detection schemes, vehicles entering facilities such as military bases and embassies can be checked for explosives by x-ray or vapor detection, but these inspections also suffer from limitations.

What is needed, therefore, is an improved system and method for protecting against terrorism. It is to such systems, methods, and detection systems that the present disclosure is primarily directed.

SUMMARY

The present disclosure provides, in one aspect, a system and method for detection of compounds that is based on the fundamental atomic structure and characteristics of the elements contained in the Periodic Table. Disclosed embodiments are capable of detecting these elements and compounds thereof by using a unique characteristic, namely, the atomic signature of the substance being sought as determined through formulations in accordance with the present disclosure.

The unique signatures of a number of substances have been identified as part of the present disclosure, and detection systems in accordance with the present disclosure are capable of using the unique material signature for detecting and locating the substance of interest. The detection systems according to the present disclosure are capable of detecting target substances at variable distances based on the atomic structure of the target sought and the mass of that target. The larger the mass, the longer the distant of detection. Among other substances, targets have included hydrochloric acid, formaldehyde, lead, cobalt, gunpowder, and various other explosives and compounds.

These and other features of the present disclosure will become more apparent upon reading the following specification in conjunction with the accompanying drawing figures.

BRIEF DESCRIPTION OF THE DRAWINGS

Various aspects of the present disclosure are described herein below with reference to the accompanying figures.

FIGS. 9A$i$-9A$iii$ is a chart of characteristic data used to compute frequency values of common elements and materials in accordance with the present disclosure.

FIGS. 9B$i$-9B$ii$ is a continuation of the chart of FIGS. 9A$i$-9A$iii$.

FIG. 9C is a further continuation of the chart of FIGS. 9A$i$-9A$iii$.

FIG. 10 is a chart of computed frequency values of the Earth based on latitude.

DETAILED DESCRIPTION

Figure 1:
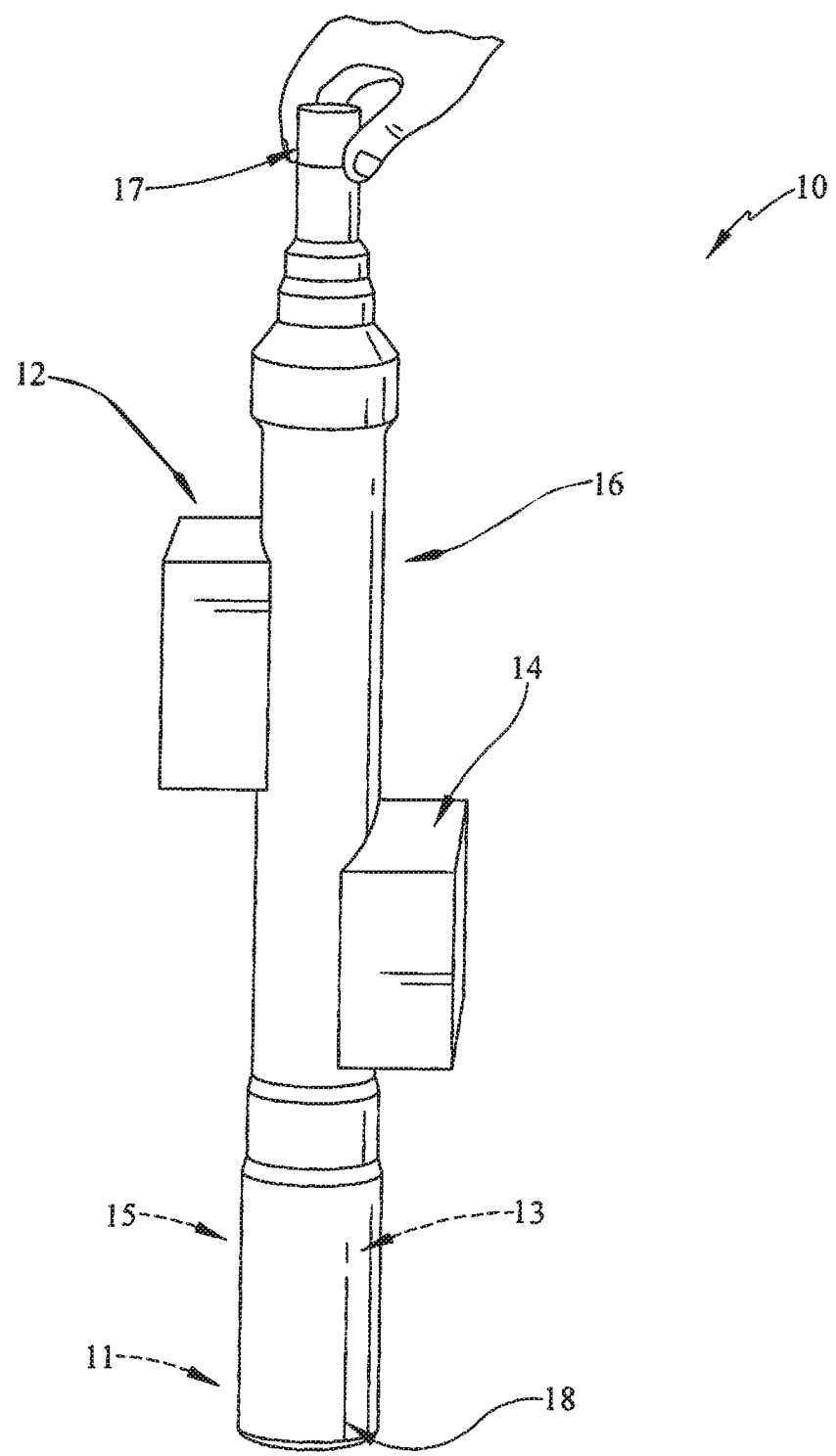
FIG. 1 is a perspective view of one exemplary embodiment of a detection system in accordance with the present disclosure.

The present disclosure can be more readily understood by reference to the following detailed description of embodiments of the disclosure and the examples included herein. Before the embodiments are disclosed and described, it is to be understood that the present disclosure is not limited to the embodiments described within this disclosure. Numerous modifications and variations therein will be apparent to those skilled in the art and thus remain within the scope of the present disclosure. It is also to be understood that the terminology used herein is for the purpose of describing specific embodiments only, and is not intended to be limiting.

Unless otherwise noted, the terms used herein are to be understood according to conventional usage by those of ordinary skill in the relevant art. In addition to the definitions of terms provided below, it is to be understood that as used in the specification and in the claims, "a" or "an" can mean one or more, depending upon the context in which it is used.

To facilitate an understanding of the principles and features of the present disclosure, it is explained hereinafter with reference to its implementation in an illustrative embodiment. In particular, the disclosed embodiments are described in the context of being a system and method for protecting against terrorism.

The materials described hereinafter as making up the various components of the disclosed embodiments are intended to be illustrative and not restrictive. Many suitable materials that would perform the same or a similar function as the materials described herein are intended to be embraced within the scope of the present disclosure. Such other materials not described herein can include, but are not limited to, materials that are developed after the time of the development of the disclosed embodiments, for example.

All patents, patent applications and publications referred to herein are incorporated by reference in their entirety.

In one exemplary embodiment, a detection system includes a transmitter and a receiver. The transmitter is tunable to various frequencies in the ultra low and extreme low frequency ranges (such ranges are known to those of ordinary skill in the art). The transmitter replicates a resonance (or sympathetic response) of a specific material at a specific computed frequency. The magnetic relationship, or "line", is then formed between the transmitter and the target material.

The inventor believes elements and compounds have resonating frequencies in their ambient form (that is, these frequencies are not induced by an external source but are inherent to the substance itself). This resonating frequency theory is supported by research into Nuclear Magnetic Response (NMR) and Nuclear Quadrupole Response (or NQR). It is also believed that by subjecting a particular substance to an externally generated radio frequency (RF) wave at the corresponding resonant frequency, an electromagnetic response in the form of another RF wave can be generated from the targeted substance. For example, a particle may be overrun with the transmitted RF wave, forming an isotope (adding one or more electrons) and become momentarily unstable to emit responsive RF waves. The responsive RF wave produces enough noise to be recorded using the receiver antenna. It is also possible that a magnetic relationship (line) exists between common elements and common compounds.

The receiver is designed to detect an RF wave coming back from the target and/or the magnetic line of the material. Aligning the detection system toward the material provides a signal to the user for determining a line of bearing to the target of interest. Through triangulation, the specific location of the target material can be identified. The transmitter is designed to produce electromagnetic radiation (such as a radio wave) having a frequency based on the calculated value for the specific material of interest. In one illustrative embodiment, one or more calculated frequencies is proportional to the (i) proton number, (ii) neutron number, and/or (iii) atomic mass of the material of interest are used. In another embodiment, this calculated frequency is proportional to the combined neutron number and atomic mass. In some embodiments, the frequencies can be magnified by one or more orders of magnitude. In some embodiments, various voltages can be used in producing the transmit frequency.

Figure 2:
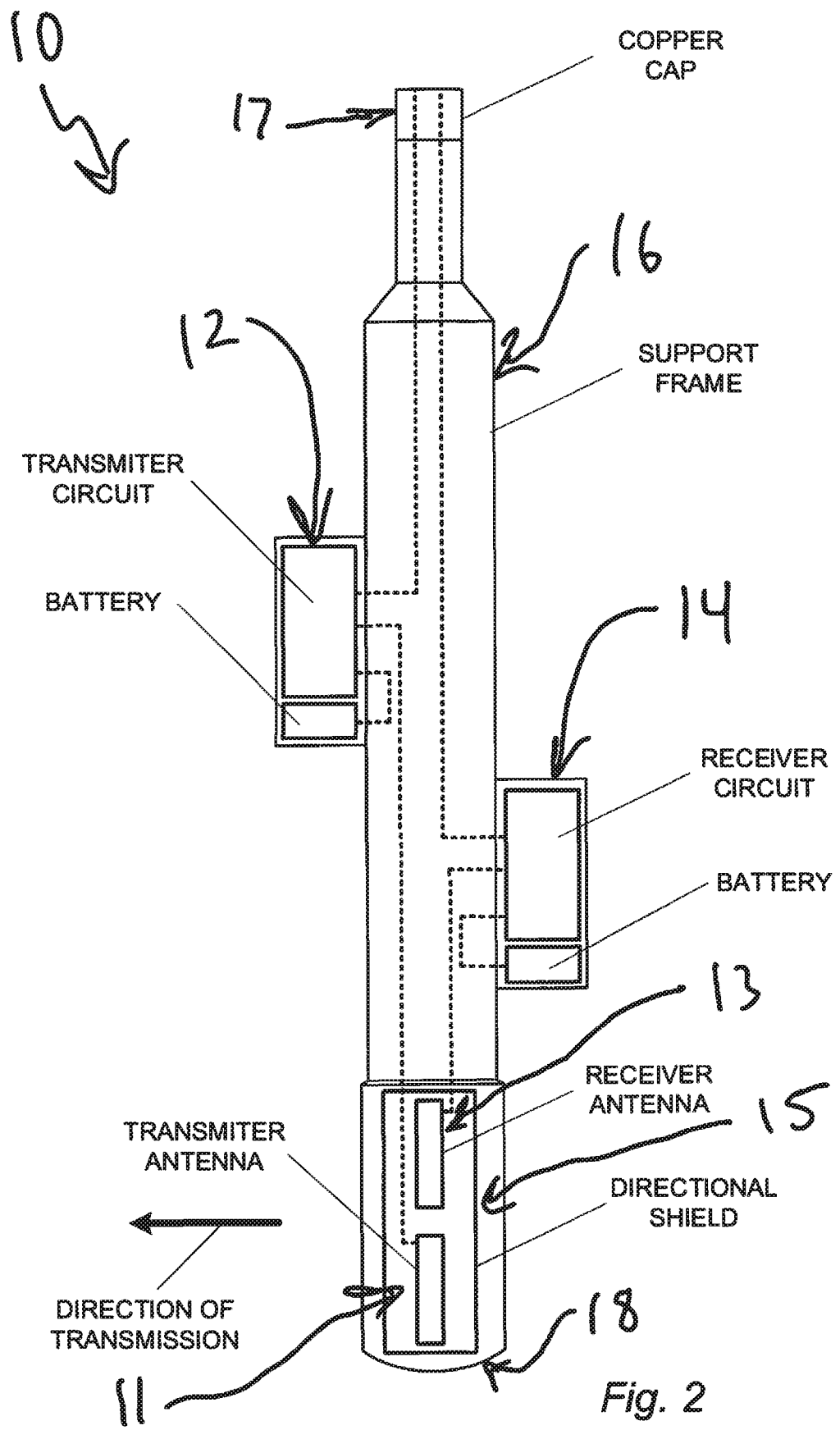
FIG. 2 is a diagrammatic sectional view of the detection system of FIG. 1.
Figure 3:
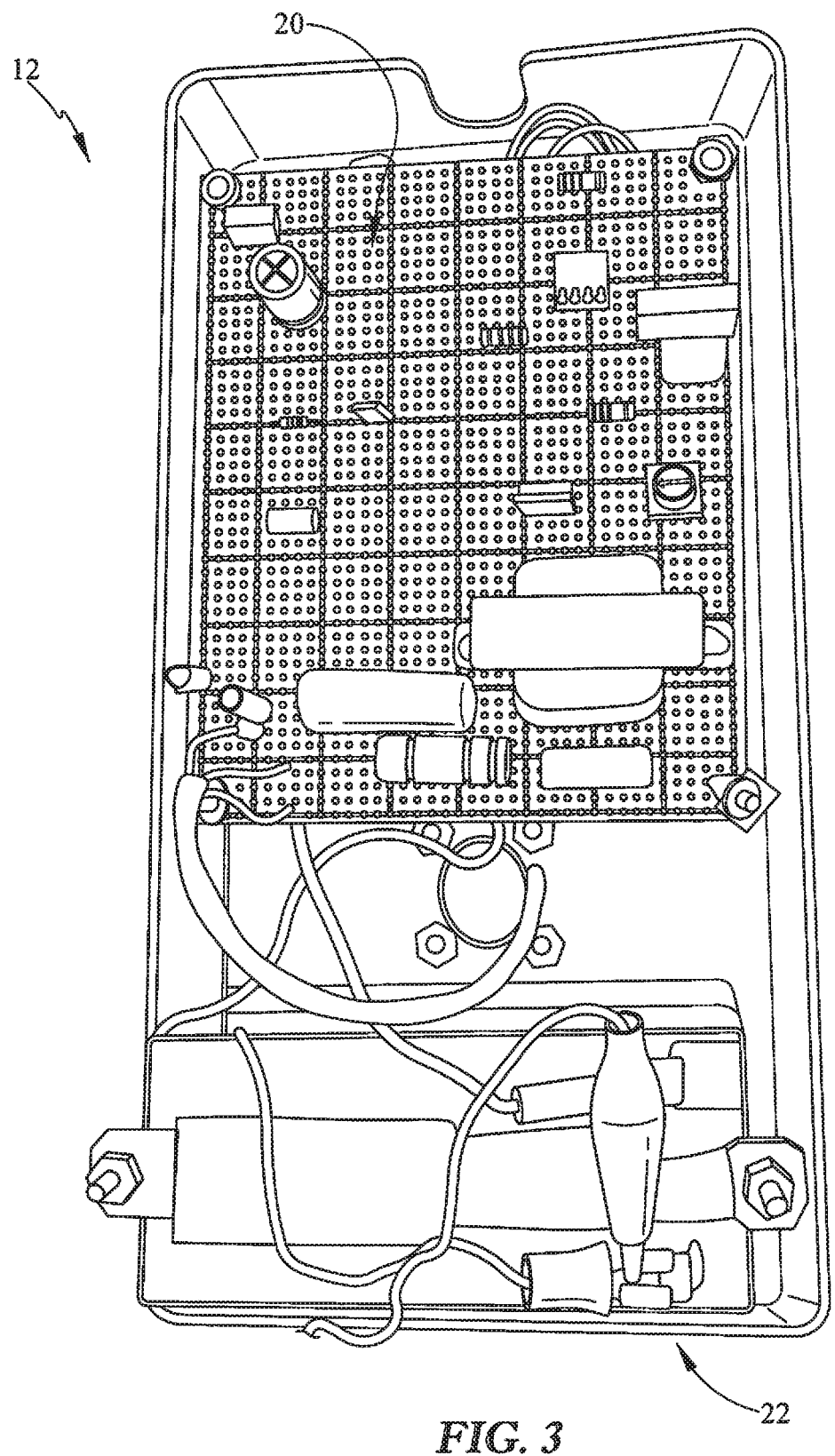
FIG. 3 is a perspective view of a transmitter circuit board of the detection system of FIG. 1.
Figure 4:
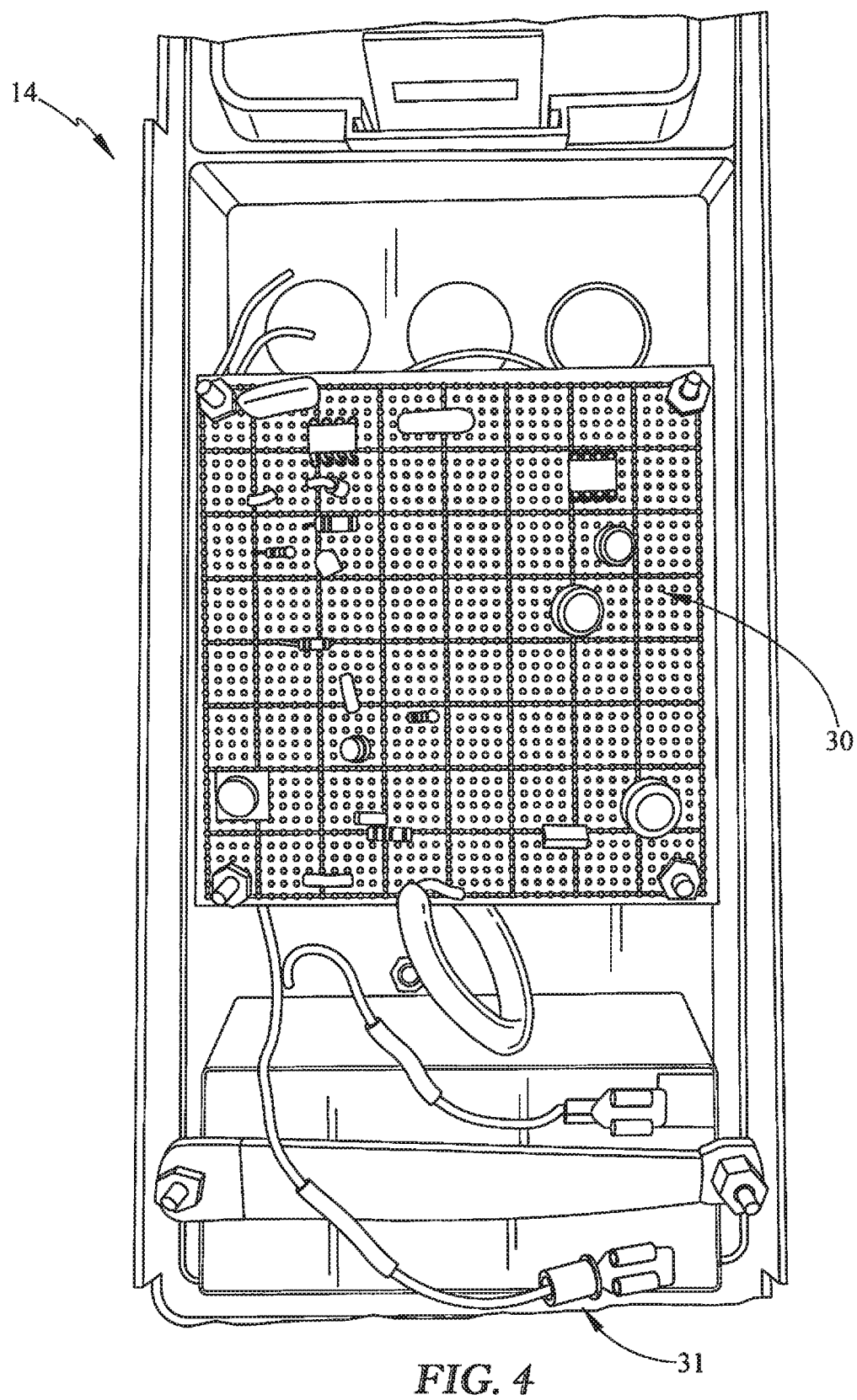
FIG. 4 is a perspective view of a receiver circuit board of the detection system of FIG. 1.
Figure 5:
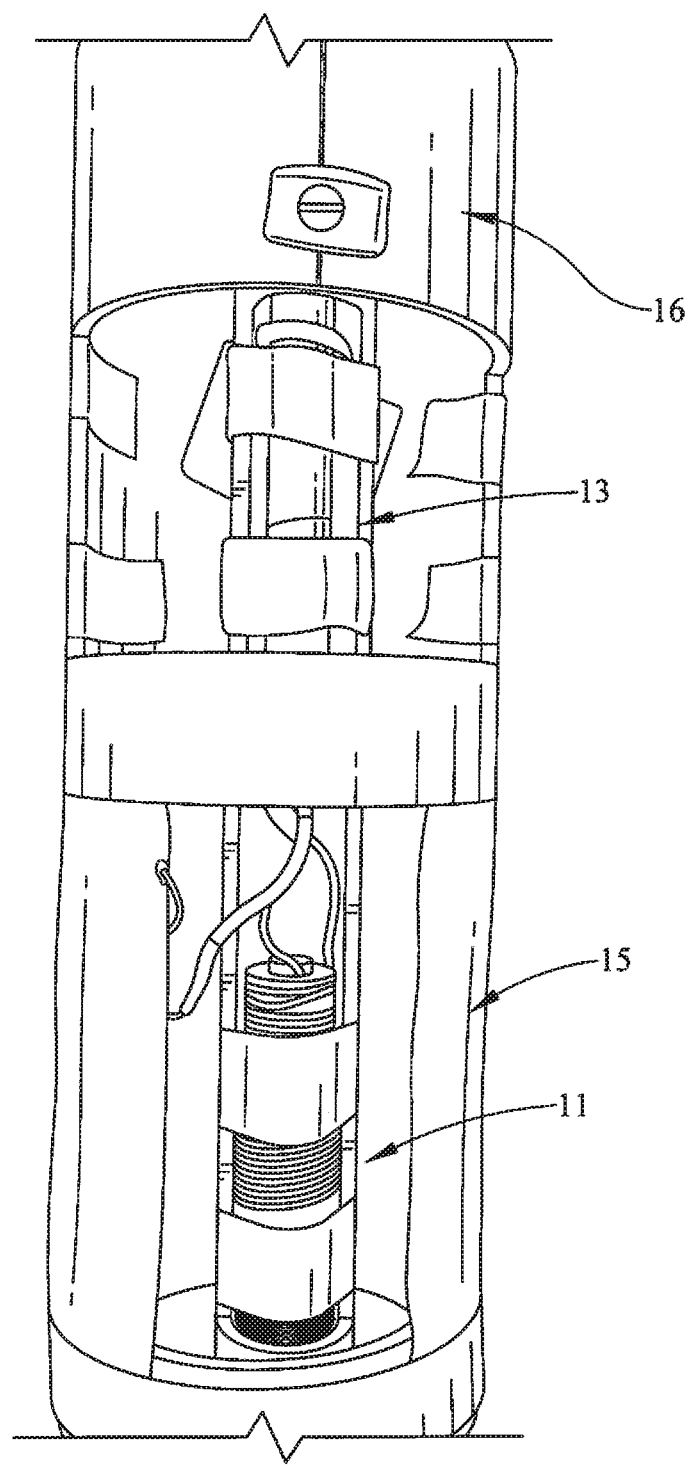
FIG. 5 is a perspective view of receiver and transmitter antennas received in a directional shield of the detection system of FIG. 1.

As shown in FIG. 1 in one exemplary embodiment, a detection system 10 includes a transmitter unit 12 and a receiver unit 14 that is attached to a support frame 16 (in this illustrative embodiment, a set of interconnected PVC pipes). A transmitter antenna 11 and a receiver antenna 13 are housed in the lower portion of the support frame 16. A directional shield 15 at least partially surrounds the antennas 11, 13 to provide directionality for the detection system 10. The frame 16 can be capped at an upper end with a copper cap 17 and at a lower end with a base cap 18. The internal structure of the detection system 10 is schematically shown in FIG. 2. One embodiment of a transmitter unit 12 is shown in FIG. 3. One embodiment of a receiver unit 14 is shown in FIG. 4. One embodiment for the arrangement of antennas 11, 13 and directional shield 15 is shown in FIG. 5.

Figure 6:
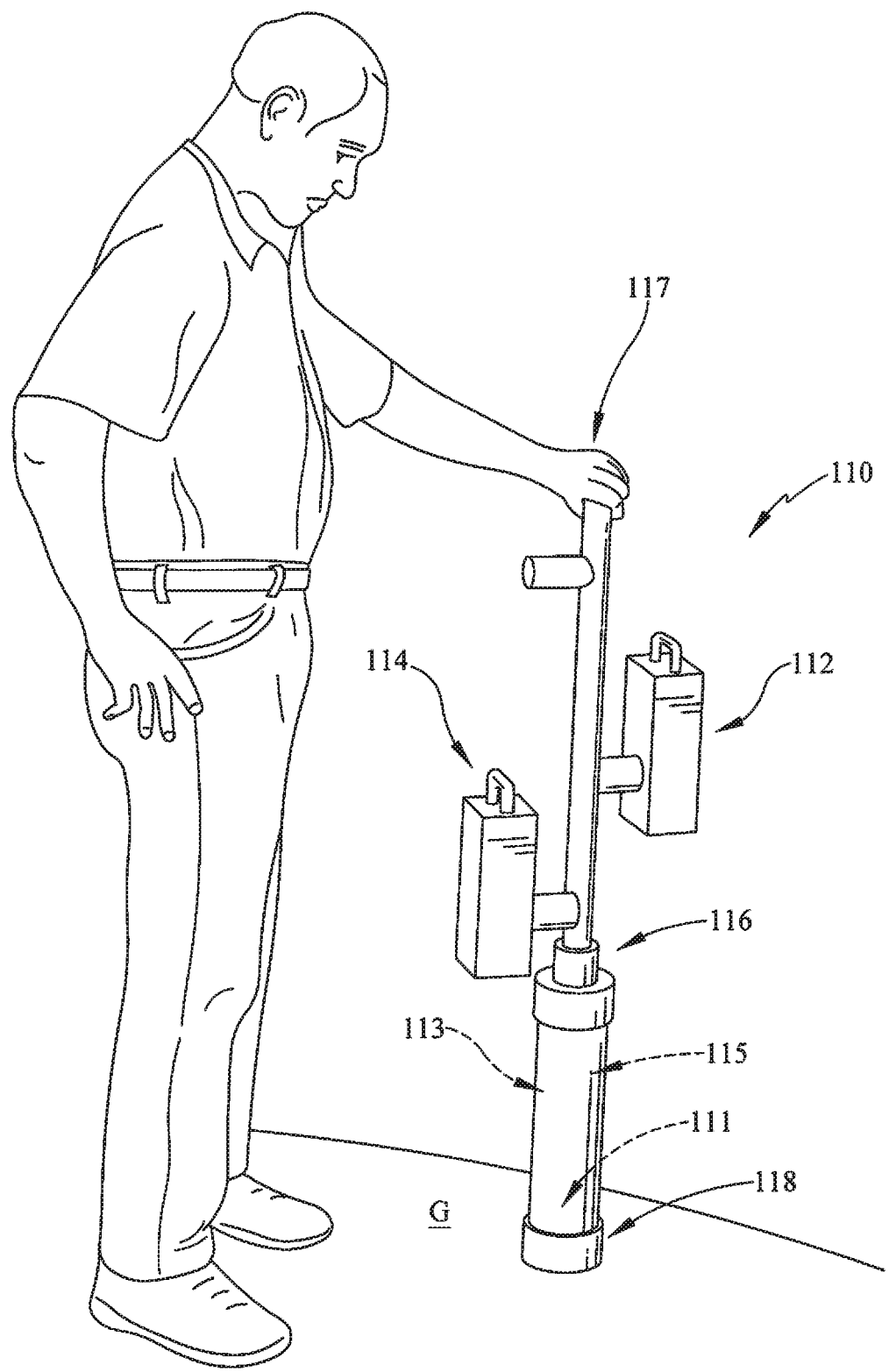
FIG. 6 is a perspective view of another exemplary embodiment of a detection system in accordance with the present disclosure.

Another embodiment of a detection system 110 in accordance with the present disclosure is shown in FIG. 6. The detection system 110 is similar to detection system 10 shown in FIGS. 1 and 2, with similar reference numerals in the 100's used to identify similar components. The detection system 110 includes a frame 116 formed from PVC pipe (or pipe or tube made of any suitable material) approximately 40 inches long. The lower approximately 12 inches of the frame 116 is approximately four inch diameter PVC pipe, while the rest of the central pipe unit is formed of 1 ½ inch PVC pipe. In some embodiments, contact between the detection system 10 and the ground G, such as shown by detection system 110 in FIG. 6, can increase the detection capabilities of the detection system 10 as the Earth may provide a medium for transmitting the signal and detecting a response. The supporting ground G of the detection system 10 can be Earth, concrete, asphalt, plastic, or other similar substance, and the ground G should be a fairly homogenous substance with a flat surface for at least approximately 4 inches in all directions. Thus, if used on Earth, there should be minimal grass, roots, or other materials immediately adjacent to or beneath the contact point between the detection system 10 and the ground G. Likewise, if used on a concrete sidewalk, there should be no reinforcement bar directly beneath the point of contact. To ensure smooth rotation of the detection system, a bearing pad or cup should be placed on the ground and the detection system rested on that pad or cup.

Figure 7:
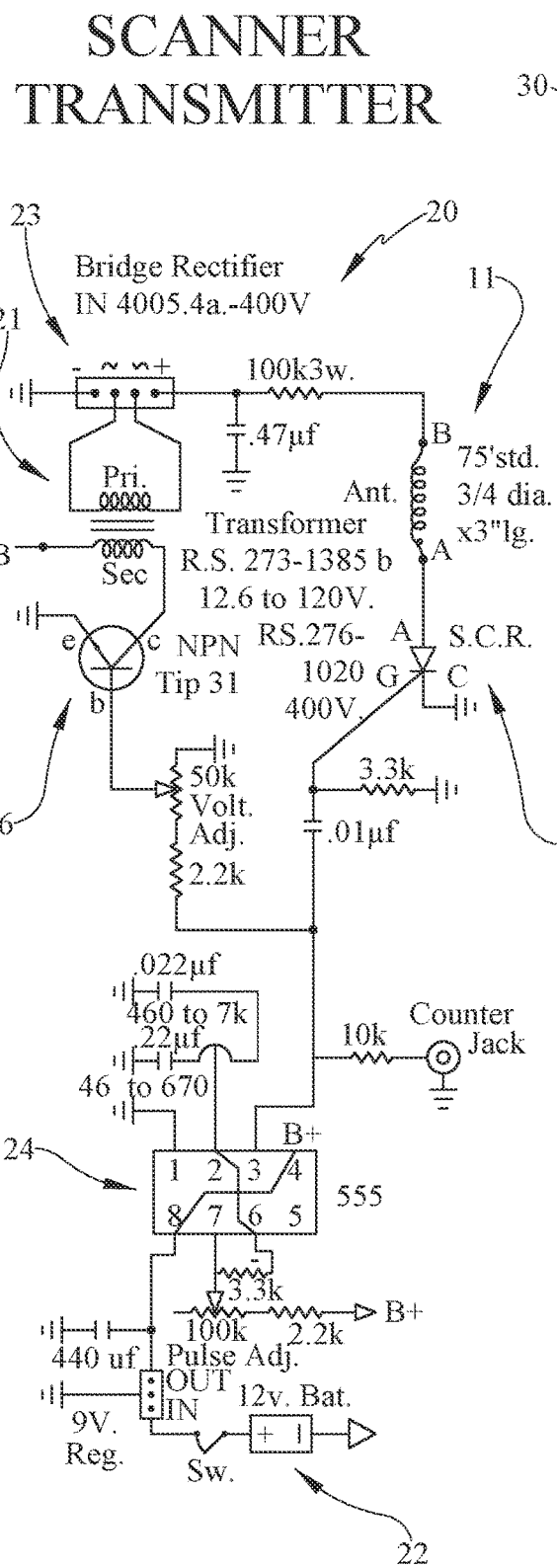
FIG. 7 is a schematic view of one exemplary embodiment of a transmitter circuit according to the present disclosure.

In the illustrative embodiment, the transmitter 12 can include the electronic circuit 20 of FIG. 7, powered by a battery 22 (e.g., 12 volt, 1.2 amp battery) with a regulated output of nine volts. The transmitter circuit 20 can use a 555 timer 24 as a tunable oscillator to generate a pulse rate. The output of the oscillator is fed in parallel to an NPN transistor 26 and a silicon controlled rectifier (SCR) 28. The transistor 26 is used as a common emitter amplifier stage driving a transformer 21. The transformer 21 is used to step up the voltage as needed.

The balanced output of the transformer 21 feeds a bridge rectifier 23 as shown in FIG. 7. The rectified direct current flows through a 100 K, three watt resistor to terminal B of the transmitter antenna 11. A plurality of resistors and capacitors fills in the circuit 20. In some embodiments, the transmitter antenna 11 can be formed from a coil of about 25 meters of 14 strand wire tightly wound around a one centimeter PVC core. The transmitter antenna 11 can be, in one exemplary embodiment, in a 1"×3" configuration at a bottom end of the frame 16 as suggested in FIG. 5.

In the illustrative embodiment, the transmitter antenna 11 is shielded approximately 315 degrees with the directional shield 15 (illustratively formed from aluminum and copper leaving a two inch opening) as suggested in FIG. 5. Terminal A of the antenna 11 is switched to ground through the SCR 28 as shown in FIG. 7. The SCR 28 is "fired" by the output of the 555 timer 24. This particular configuration generates a narrow pulsed waveform to the antenna 11 at a pulse rate as set by the 555 timer 24. Power is delivered through the 3 W resistor. Frequencies down to 4 Hz are achieved by an RC network containing a 100 K pot, a switch, and one of two capacitive paths.

The circuit 20 provides simple RC-controlled timing and delivers pulses to the primary of a step-up transformer, the output of which is full-wave rectified and fed to the transmitter antenna 11. The pulse rate is adjustable from the low-Hz range to the low-kHz range. The sharp pulses at low repetition frequency yield a wide spectrum of closely spaced lines. The pulse rate is adjusted depending on the material to be detected.

In the illustrative embodiment, the receiver antenna 13 can be formed from an approximately 3 inch long segment of a' inch diameter hollow copper pipe as suggested in FIG. 5. In some embodiments, a short (approximately 4 centimeters long) segment of a one centimeter diameter hollow copper pipe forms the receiver antenna 13. The receiver antenna 13 can likewise be located in the lower portion of the frame 16 directly above the transmitter antenna 11. In some embodiments, the receiver antenna 13 is connected to the receiver unit 14 via a shielded cable.

Figure 8:
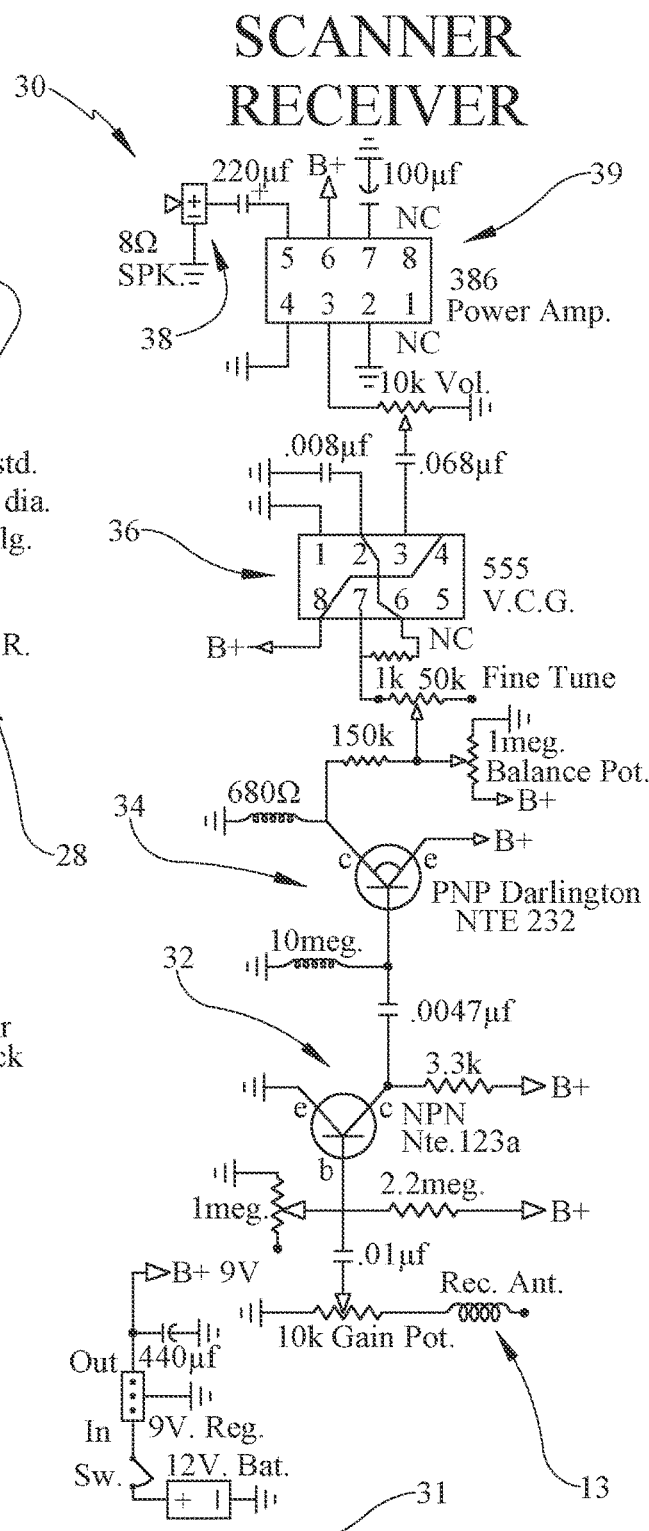
FIG. 8 is a schematic view of one exemplary embodiment of a receiver circuit according to the present disclosure.

In the illustrative embodiment, the receiver unit 14 can include the electronic circuit 30 of FIG. 8. Voltage from the receiver antenna 13 passes through a 10 K gain pot to an NPN 200 transistor 32 used as a common emitter. The output is capacitively coupled to a PNP Darlington transistor 34. A plurality of resistors and capacitors fills in the circuit 30. The output is fed through a resistor potentiometer network to a 555 timer 36 that is used as a voltage-controlled oscillator. A received signal of given amplitude generates an audible tone at a given frequency. The output is fed to a tone generator 38 (such as a speaker) via a standard 386 audio amp 39. The emitted sounds are reminiscent of those of a standard metal detector, but with significantly greater variability in pitch and harmonic content. Sounds can be categorized as "grunts," "whines," and a particular form of whine with a higher harmonic notably present. In some embodiments, another indicator of a received signal is used, such as light, vibration, digital display, or analog display, in alternative to or in combination with the sound signal. A battery 31 can be used to power the receiver circuit 30.

The receiver circuit 30 utilizes a coherent, direct-conversion mixer (homodyne) with RF gain, yielding a baseband signal centered about DC. After a baseband gain stage, the baseband signal is fed to another timing circuit that functions as a voltage-controlled audio-frequency oscillator. The output of this oscillator is amplified and fed to a speaker.

Various aspects of the circuit are unconventional in the eyes of an experienced circuit designer. For example, the received signal passes through a 10 K ohm potentiometer before it is detected, which practice would ordinarily be avoided based on signal-to-noise considerations. As another example, the bias point of a particular amplifier transistor would appear to make the detection system susceptible to desensitization by 60-Hz interference. These kinds of non-standard practices are ordinarily "cleaned up" by investigators attempting to reproduce the phenomenon but should only be done after developing a sound understanding of those effects that contribute to the function.

The transmitter antenna 11 and receiver antenna 13 are axially aligned with one another as suggested in FIGS. 2 and 5. Supplying voltage to the transmitter antenna 11 produces a resonant inductive coupling with the receiver antenna 13. For example, a magnetic field generated by the transmitter antenna 11 induces a voltage to be produced by the receiver antenna 13 to generate a baseline output signal to the operator (such as an audio signal of a specific tone). In some embodiments, the receiver circuit is replaced by a dowsing rod that responds to the material stimulated by the transmitter circuit by providing a line of bearing to the human operator sensitized by physical contact with the transmitter radiating at a frequency appropriate for the material of interest. In still other embodiments, the transmitter is replaced by physical contact with a specific number of metallic objects (e.g., small segments of wire), where the number of objects corresponds to the frequency that corresponds to the material of interest.

The transmitter 12 also generates a wave pulse at a specified frequency that is transmitted directionally into the ground G. The generated frequency is closely approximate or exact to that of the target material, and that relationship creates a responsive RF wave and/or a magnetic line between the transmitter antenna 11 and the target. When the detection system 10 is aligned with a target material (e.g., when the opening of the directional shield 15 is pointing toward the target material), the voltage produced by the receiver antenna 13 changes and thereby produces a detection output signal (e.g., an audio signal having a tone different than that of the baseline). While the specific mechanism is not completely understood, it is believed that a reflective wave is produced by the target material that amplifies, resonates, off sets, or otherwise modifies the magnetic field passing through the receiver antenna 13 to alter the voltage produced thereby in generating the output signal. Said another way, it may be that the receiver antenna 13 is responding to a voltage increase from the transmitter antenna 11 swinging over the magnetic line to the material. Thus, it will be understood by those of skill in the art that the receiver antenna 13 may not "receive" a signal in a traditional sense. That change in voltage generates a signal back to the receiver unit 14, which generates the detection output signal.

By way of such an example, it has been suggested that perhaps the underlying physics being exploited is nuclear quadrupole resonance (NQR). Counter to this explanation it may be argued that the pulse repetition frequencies of the detection systems in accordance with the present disclosure bear no obvious relationship to the typical NQR frequencies for substances of interest (low MHz), and furthermore that the detection ranges without any intentional interference suppression at all are completely unrealistic for an NQR explanation. However, the waveform produced by the detection systems does contain a broad spectrum of frequencies, spaced reasonably close in terms of typical NQR frequencies and line widths. Also, frequency conversion at some point via nonlinear effects could play a role. With respect to the large observed detection distances, serendipitous alignment of several waveform harmonics—or of generated intermodulation products—with several resonance frequencies of one compound may improve the interaction somewhat. And, as explained herein, earth resonances may contribute to the range of the detection systems. This discussion is not in any way intended to identify NQR as the physical basis of the detection system, but is intended to illustrate the kind of unintended or unforeseen circumstances that may eventually connect the operation of the detection systems in accordance with the present disclosure to some established physical phenomenon.

There is a significant possibility that various spectral lines in the waveform are coupling to higher-order earth-resonance modes (e.g., Schumann Resonances discussed in J. D. Jackson, Classical Electrodynamics, 2nd Ed., John Wiley & Sons, 1975, pp 360f). Nikola Tesla utilized such resonances in the early part of the 20th century to efficiently transmit electrical power wirelessly across large distances. Such an effect could be a significant factor in the detection system's operation, and samples be placed on or near the earth may be easier to detect (though detections may still be obtained for elevated samples).

A method according to one exemplary embodiment of the present disclosure includes the use of the standard atomic structure of a material to calculate the resonant frequency to which a particular substance would generate or respond. Each element and compound comprises a definable atomic structure composed of the total number of protons and neutrons of that target material. This unique nuclear composition of every substance makes it likewise uniquely identifiable and detectable. The manner in which this information is applied thus enables the detection of any target substance.

A target material can be detected and located based on a resonant (believed to be responsive RF wave and/or magnetic) relationship between the target and a transmitter 11 transmitting at the frequency specific and unique to the target material. The transmitter unit 12, through the transmitter antenna 11, appears to induce a resonance (due to responsive RF waves and/or magnetic and/or otherwise yet to be explained effects) in a targeted material to resonate at a specific computed frequency. The receiver antenna 13 and receiver circuit 14 appears to detect the resonance induced in the material and in so doing indicates the approximate line-of-bearing to the material. The primary method used by this detection system to detect specific materials is based on tuning the circuit of the transmitter to a specific value that is computed for the material of interest. The frequency can be based on any of the three defining characteristics of the substance, the number of protons, number of neutrons, or the atomic mass (sum of protons and neutrons), and combinations thereof. The frequency can be transmitted at varying voltages to compensate for other external effects or interference. The tables in FIGS. 9A-9C illustrate characteristics of common materials used to calculate the resonant frequencies. To accomplish this tuning, the frequency of the signal from the transmitter antenna 11 is essentially set to some harmonic of the elements of the material.

According to one method, a frequency for transmission is selected for a particular element based on the number of protons, number of neutrons, and/or atomic mass (sum of protons and neutrons) for the element. For example, the selected frequencies for Arsenic (As) would be 33 Hz (based on number of protons), 42 Hz (based on number of neutrons), and 75 Hz (based on atomic mass) as suggested in FIGS. 9A$i$-9A$iii$. These frequencies can also be increased by one or more orders of magnitude (10×, 100×, etc.). Similarly, the frequencies for a compound can be selected based on the sum total of the constituent parts. For example, a Formaldehyde molecule has a combined total of 16 protons (corresponding to a frequency of 16 Hz), 14 neutrons (corresponding to a frequency of 14 Hz), and mass of 30 (corresponding to a frequency of 30 Hz). Individual scans using two or more of these frequencies can be used to uniquely identify the element or compound.

According to another method, a frequency is selected for a particular element based on the sum of the number of protons and atomic mass (sum of protons and neutrons) for the element. For example, the selected frequency for Arsenic (As) would be 108 Hz based on the addition of 33 (protons) with 75 (atomic mass) as suggested in FIGS. 9A$i$-9A$iii$. This frequency can also be increased by one or more orders of magnitude (10×, 100×, etc.). Similarly, the frequency for a compound can be selected based on the sum total of the constituent parts. For example, a Formaldehyde molecule has a combined total of 16 protons and mass of 30. The corresponding frequency would be 46 Hz (addition of 16 (protons) with 30 (mass)).

As another example, smokeless gun powder would yield a base transmit frequency of 1160. The tuning frequency of 1160 Hz is derived from the chemical composition (discrete atomic structure) CH2NO3CHNO3CH2NO3 for nitroglycerin. By using the atomic number, or number of protons for each element, the frequency is calculated as: $6+(1*2)+7+(8*3)+6+1+7+(8*3)+6+(1*2)+7+(8*3)$ which yields a sum of 116 protons in the compound. This is then increased by an order of magnitude (10×) yielding 1160 Hz as the frequency to use to search for nitroglycerin.

Some elements and compounds may have overlapping frequencies using only one of the methods described above, and it can be beneficial to use multiple of the above described methods when searching for or identifying a target material.

As noted above, the transmission of the frequency wave may be through contact with the Earth. The Earth can, thus, be the medium through which a "connection" between the detection system and the target substance is established. When a connection is established, a change in the energy output of the transmitter 11 is detected by the "receiver" 13. This is then relayed to an audible output detection system 38, or other signaling detection system.

The distances over which detection is possible are based on the amount of substance to be located and its unique nature. Common materials as water, sand, salt, etc., cannot be singularly located due to the sheer abundance in which they exist on Earth. However, for other more discernable substances, embodiments of the present disclosure are capable of locating materials based on their weight with a detection of 1 ounce of material at a range of up to approximately 660 feet. The detection range appears to vary directly with weight. Thus, a 2 ounce material can be detected up to approximately 1320 feet.

It is believed that materials radiate their harmonic resonance frequency in response to a matching transmitted frequency. This radiated RF response is transmitted to and through the Earth immediately when the material is stimulated by the externally generated transmitted radio frequency (RF) wave. It has been observed that this may create a "footprint" of induced resonant response in the ground which may remain for some time, depending on the mass and other characteristics of the material. The apparatus of the present disclosure may continue to detect this footprint for some time after the target substance is removed.

A process called "cleansing a line" has been developed to remove the "footprint line" of materials that had been detected, but then removed. This cleansing process utilizes the natural Earth frequency at the specific location as refined by latitude and time of year as related to the position of the sun, to transmit a frequency to "erase" the connection line. A separate set of frequencies based on latitude are illustrated in FIG. 10.

Due to the ultra low frequencies and power requirements of the detection system of the present disclosure, the operation and performance are quite susceptible to a number of factors that are still under investigation. For example, in some embodiments, the detection system 10 can require continual human contact through the top copper cap 17 for consistent readings. There is a phenomena of capacitance or impedance of the human body that has yet to be fully defined. This applies to not only the detection of the response RF wave and/or magnetic line, but also lends to false readings when the transmit direction is aligned with the operators body. Thus, by standing on the opposite side of the detection system from the intended target, such as shown in FIG. 6, the body will not interfere with the signal. In addition, the copper cap 17 can be connected to the grounds of the transmitter and/or receiver circuits 20, 30 (as suggested in FIG. 2) in order to minimize interference from a operator holding and operating the detection system.

In other embodiments, human contact is not required for accurate readings. The operator should still remain opposite from the transmit direction of the detection system to avoid possible interference. As noted the human body has its own magnetic properties and can interfere with the detection ability of the device.

Additionally, large equipment operating nearby or high voltage overhead or underground lines can disrupt operation of the disclosed embodiments by distorting the RF wave and/or "connection line" or disrupting them altogether.

In the illustrative embodiment, the detection system 10, when rotated, should be kept vertical. Rotations are in approximate 70-80 degree increments due to body influence and increments are advanced in a clockwise or counter-clockwise direction providing a full 360 degree sweep when trying to locate target materials. Determination of the bearing angle in this way from two or more locations then allows the location of the target substance to be estimated by triangulation. The detection system 10 can remain in a stationary location for tracking materials passing by.

Figure 12:
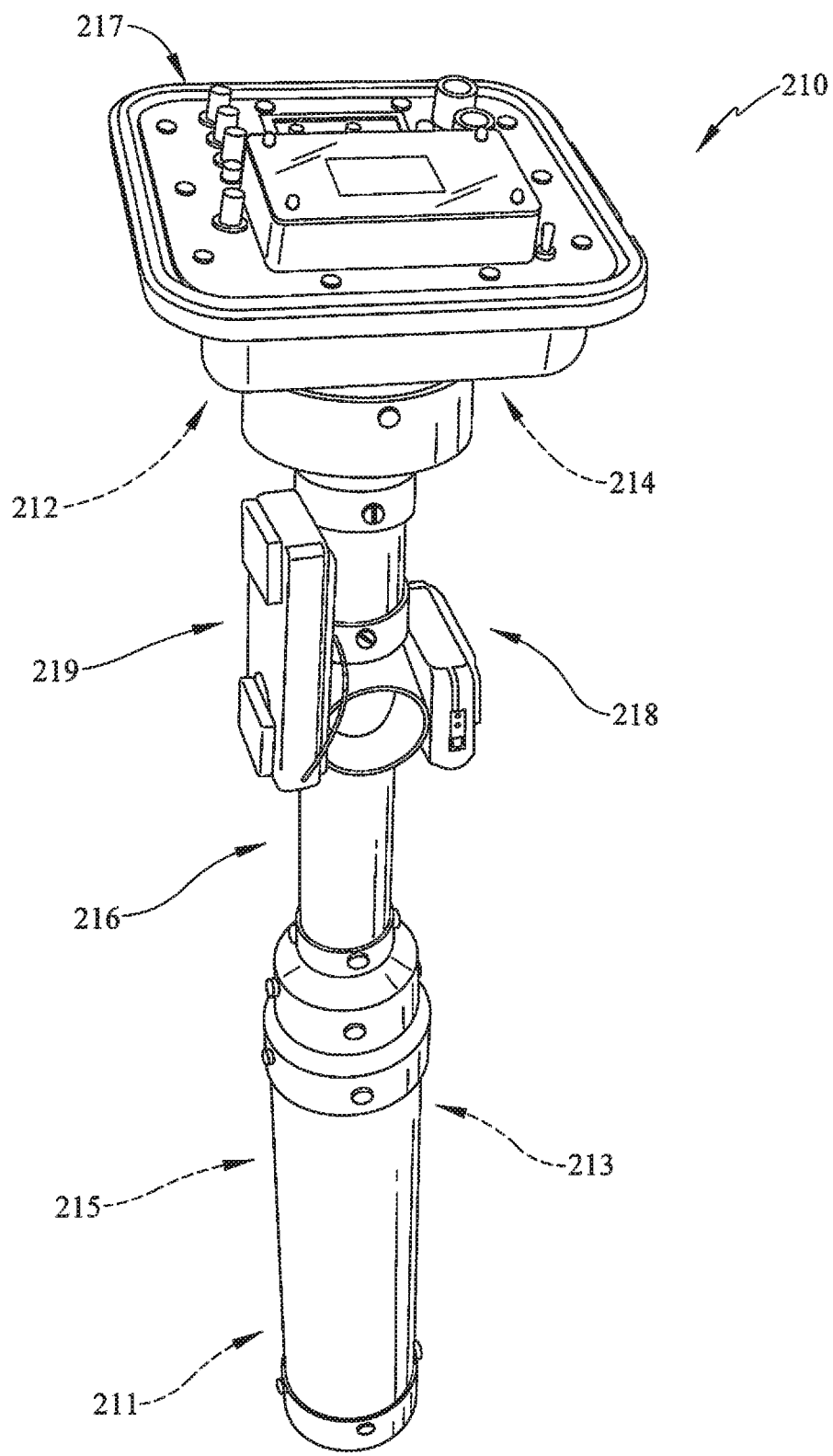
FIG. 12 is a perspective view of another exemplary embodiment of a detection system in accordance with the present disclosure.
Figure 13:
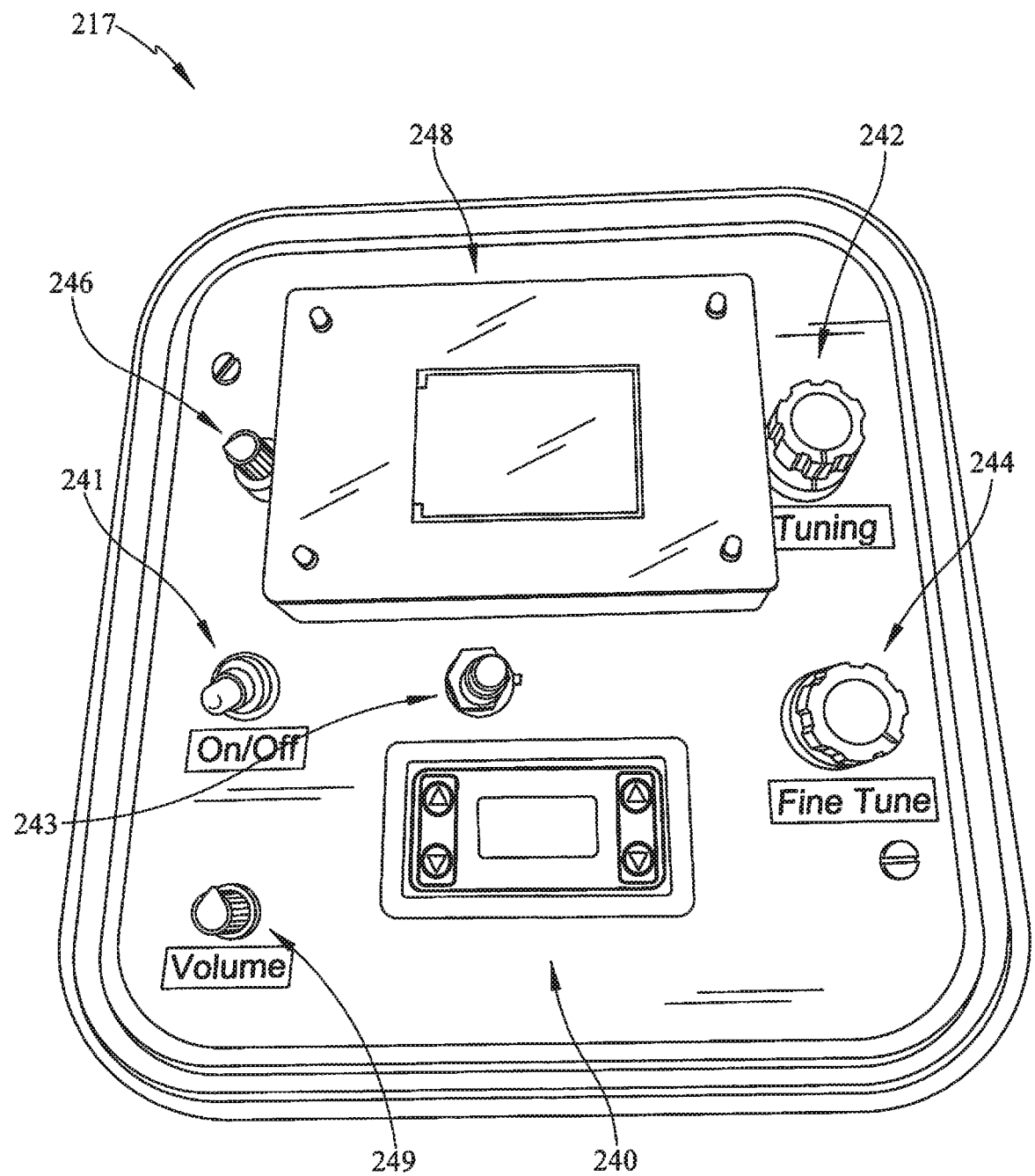
FIG. 13 is a top plan view of a control panel of the detection system of FIG. 12.
Figure 14:
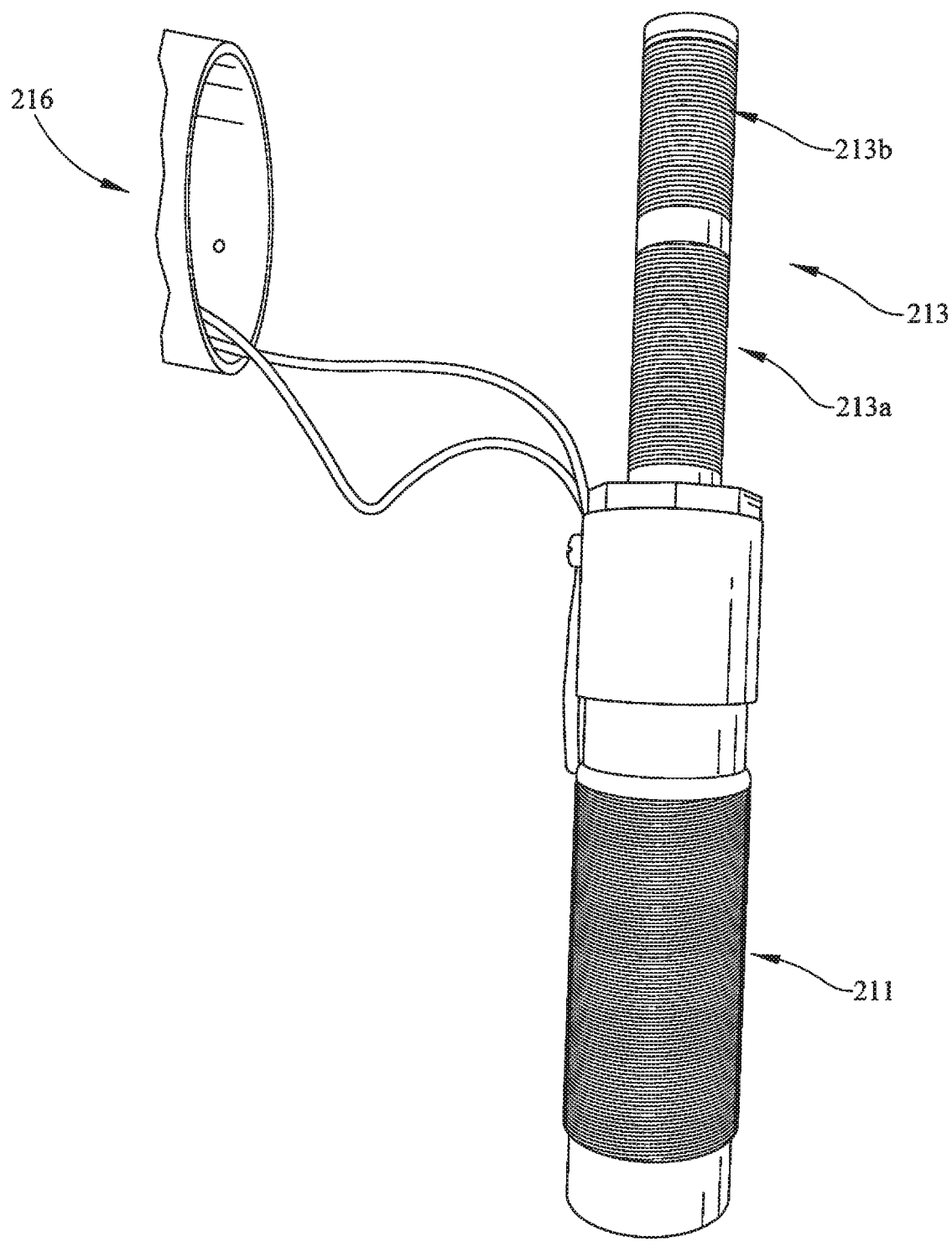
FIG. 14 is a side elevation view of transmitter and receiver antennas of the detection system of FIG. 12.

Another exemplary embodiment of a detection system 210 in accordance with the present disclosure is shown in FIGS. 12-14. The detection system 210 is similar to the detection system 10, and includes a transmitter unit 212 and a receiver unit 214 that is attached to a support frame 216 (in this illustrative embodiment, a set of interconnected PVC pipes). A transmitter antenna 211 and a receiver antenna 213 are housed in the lower portion of the support frame 216. A directional shield 215 at least partially surrounds the antennas 211, 213 to provide directionality for the detection system 210. A control panel 217 is mounted on the frame 216 and provides an operator with control of the detection system 210, including adjusting various settings and signaling the operator of a detected material. In the illustrative embodiment, a rechargeable battery 218 powers the detection system 210, including the transmitter unit 212, receiver unit 214, and control panel 217. In some embodiments, multiple batteries are used. A tone generator 219 (such as a speaker) is mounted to the frame 216 and provides audible signals to the operator for detecting target materials.

Figure 15:
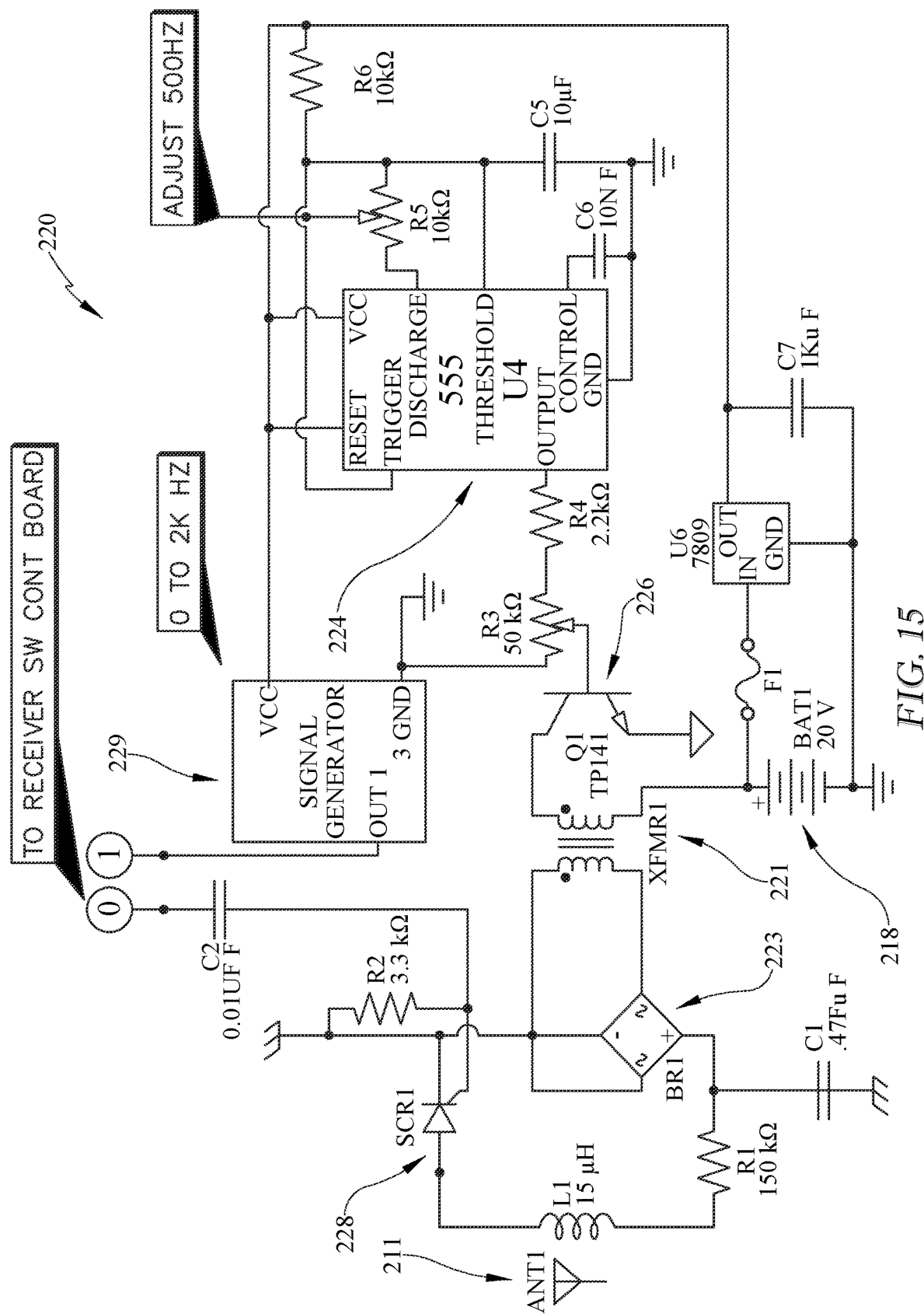
FIG. 15 is a schematic view of another exemplary embodiment of a transmitter circuit according to the present disclosure.

In the illustrative embodiment, the transmitter unit 212 can include the electronic circuit 220 of FIG. 15. Power to the circuit 220 can be regulated at nine volts, for example. The transmitter circuit 220 can use a 555 timer 224 as a tunable oscillator to generate a pulse rate. The output of the oscillator is fed to an NPN transistor 226 used as a common emitter amplifier stage driving a transformer 221. The transformer 221 is used to step up the voltage as needed. The output of the 555 timer 224 is also fed to a signal generator 229 that may provide signals as detailed further herein.

The balanced output of the transformer 221 feeds a bridge rectifier 223 as shown in FIG. 15. The rectified direct current flows through a resistor to the transmitter antenna 211. A plurality of resistors and capacitors fills in the circuit 220. In some embodiments, the transmitter antenna 211 can be formed from a coil of about 25 meters of 22 gauge wire tightly wound around a 2 inch PVC core. The transmitter antenna 211 can be, in one exemplary embodiment, in a 2"×4" configuration at a bottom end of the frame 216 as suggested in FIG. 14.

In the illustrative embodiment, the transmitter antenna 211 is shielded approximately 300 degrees with the directional shield 215 (illustratively formed from copper leaving a two inch opening). The antenna 211, opposite from the bridge rectifier 223, is switched to ground through silicon controlled rectifier (SCR) 228 as shown in FIG. 15. The SCR 228 is "fired" by the output of the 555 timer 224 (through the transformer 221 and bridge rectifier 223). This particular configuration generates a narrow pulsed waveform to the antenna 211 at a pulse rate as set by the 555 timer 224. In some embodiments, the pulse rate is frequency duty controlled. An output of the SCR 228 (0) is fed to a receiver circuit 230 (at (0)) as shown in FIG. 16.

In the illustrative embodiment, the receiver antenna 213 includes two antennae 213a, 213b as shown in FIG. 14. Each of the antennae 213a, 213b is formed from a length of wire tightly wrapped around a 1 inch PVC core. Each of the receiver antennae 213a, 213b can be, in one exemplary embodiment, in a 1"×3" configuration at a bottom end of the frame 216 above the transmitter antenna 211.

Figure 16:
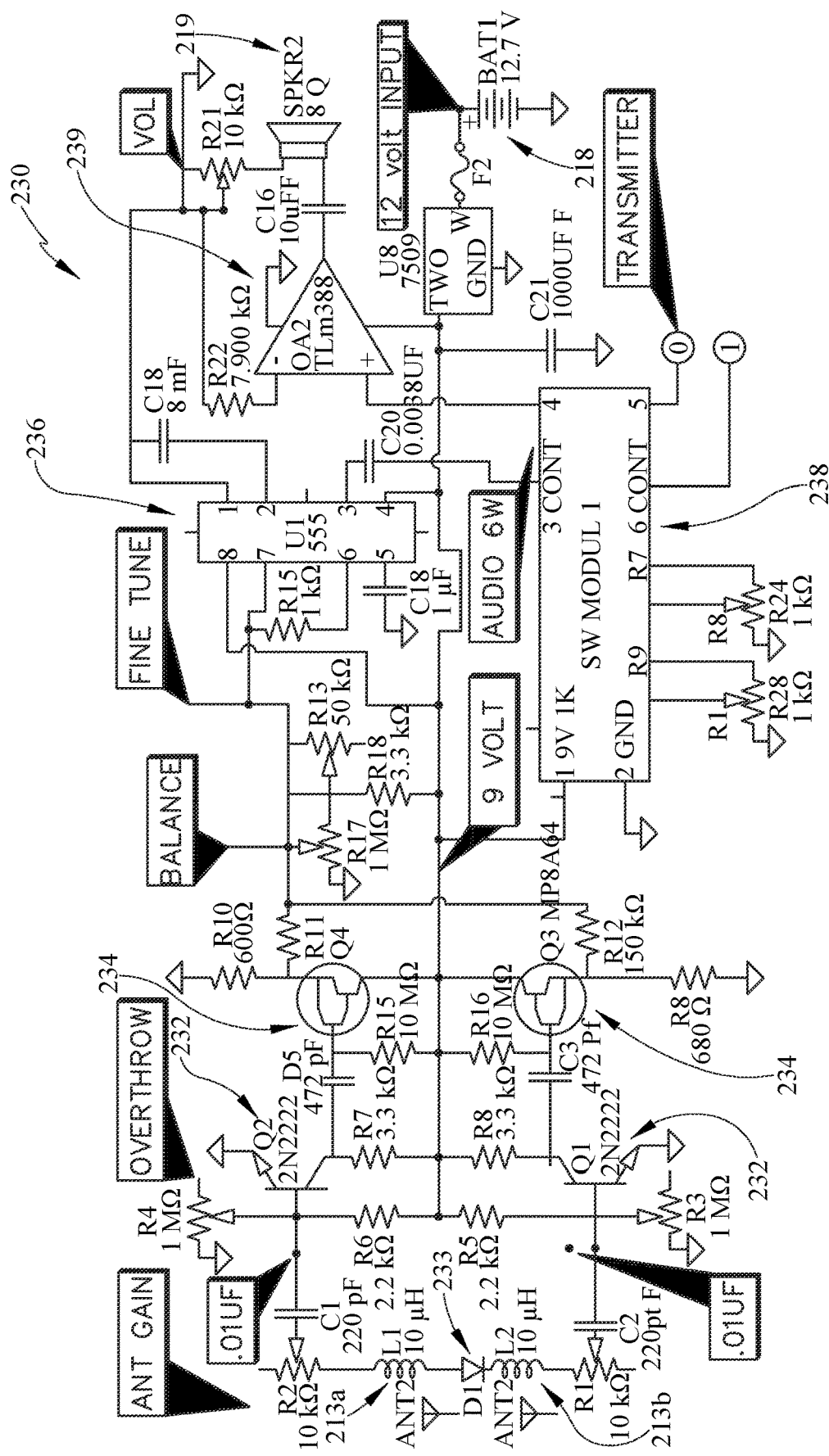
FIG. 16 is a schematic view of another exemplary embodiment of a receiver circuit according to the present disclosure.

In the illustrative embodiment, the receiver unit 214 can include the electronic circuit 230 of FIG. 16. The receiver antennae 213a, 213b are connected to a microwave high speed diode 233. Voltage from the receiver antennae 213a, 213b passes through 10 K gain pots to an NPN 200 transistors 232 used as a common emitter. The output is capacitively coupled to PNP Darlington transistors 234 for switching amplification. A plurality of resistors and capacitors fills in the circuit 230. The output is fed through a resistor potentiometer network to a 555 timer 236 that is used as a voltage-controlled oscillator. A received signal of given amplitude generates an audible tone at a given frequency. The output is fed to the speaker 219 via an audio amp 239, such as an LM386 audio amplifier. The same battery 218, or a different battery, can be used to power the receiver circuit 230. A control board 238 allows for multiple outputs from the receiver circuit 230, such as to provide dual audio outputs for the speaker 219 and a headset. In some embodiments, the transmitter circuit 220 to connect with the receiver circuit 230, such as to provide a comparative signal for use in the 555 timer 236 and/or speaker 219.

The transmitter antenna 211 and receiver antenna 213 are axially aligned with one another as shown in FIG. 14. In some embodiments, supplying voltage to the transmitter antenna 211 produces a resonant inductive coupling with the receiver antenna 213. For example, an electromagnetic induction (EMI) field may be generated by the transmitter antenna 211 and induce a voltage to be produced by the receiver antenna 213 to generate a baseline output signal to the operator (such as an audio signal of a specific tone).

The control panel 217 of the detection system 210 is shown in FIG. 13. The control panel 217 includes a transmitter frequency control 240, receiver tuning controls 242, 244, and a receiver antenna control 246. An oscilloscope 248 is coupled to the receiver circuit 230 and/or the transmitter circuit 220 to provide a visual signal to the operator for identifying target materials during operation of the detection system 210. In some embodiments, the control board 238 (at (1)) of the receiver circuit 230 and/or the signal generator 229 (at (1)) for providing the visual signal to the operator. In some embodiments, other signals/indicators of a detection can be used, such as light, vibration, digital display, or analog display, in alternative to or in combination with the sound and oscilloscope signals. The control panel 217 can also include a switch 241 for turning the detection system 210 on/off, a switch 243 for turning the oscilloscope 248 on/off, and a volume control 249 for the speaker 219.

In the illustrative embodiment, the receiving antenna can be "tuned" by adjusting the receiver tuning controls 242, 244, with the control 242 providing coarse tuning and the control 244 providing fine tuning, as shown in FIG. 13. The tuning increases or decreases the resistance to the flow of current through the receiver circuit 230 to the speaker 219, allowing unwanted feedback to be filtered and removed. The receiver antenna control 246 provides dampening to the signal received by the receiver antenna 213 such that you can have a range of full signal to no signal allowed from the receiving antenna 213. The receiver antenna control 246 works in combination with the receiver tuning controls 242, 244 to filter out unwanted signals. The transmitter frequency control 240 is digital and allows the selection of varying frequencies with up/down arrow inputs on the left side of a numeric display indicating the selected frequency. The up/down arrow inputs on the right hand side of the transmitter frequency control 240 adjust the duty cycle of the transmitted wave to allow the transmitted signal to be altered such that the upper or lower parts of the normal sine wave are adjusted. A duty cycle of 50% provides a normal sine wave for transmission. In some embodiments, the transmitter frequency control 240 is coupled to the 555 timer 224 for providing the transmitted wave of the detection system 210. In some embodiments, the transmitter frequency control 240 can break up the otherwise continuous transmission wave into equal and consistent segments such that there are uniform breaks in the transmission. In some embodiments, the transmitter frequency control 240 can be connected to the oscilloscope 248 to show the wave pattern of the transmission.

Operation of the detection system 210 is similar to that of the detection system 10 as described herein. The detection system 210 is operated at the determined frequency for the target material and rotated to identify a line of bearing to the target when a responsive signal is indicated (e.g., by audio from the speaker and/or changes on the oscilloscope). Moving the location of the detection system 210 and determining a second line of bearing allows for triangulation of the target material.

In one illustrative method for operating the detection system 210, the detection system 210 is turned on with the switch 241 as shown in FIG. 13. The transmitter frequency is set to the correct frequency for the substance or element of the target material using the up/down arrow inputs on the left side of the transmitter frequency control 240. A control sample of the target material is placed about 15-20 feet away from the detection system 210. The receiver antenna control 246 is set at about ⅓ of wide open range and the "fine" receiver tuning control 244 is set wide open. With the detection system 210 directed away from the control sample, the "coarse" receiver tuning control 242 is adjusted until the speaker 219 just starts to provide an audible output or stops providing an audible output. The "fine" receiver tuning control 244 is adjusted until the audible output stops and then adjusted back until the audible output begins. The detection system 10 is rotated until the transmit direction (e.g., opening of the directional shield 215) is pointed toward the control sample. Further tuning is required if there is no change in the audible output with the detection system 210 pointed toward the control sample as compared to pointed away from the control sample. The duty cycle for the transmit signal is set using the using the up/down arrow inputs on the right side of the transmitter frequency control 240. This can be adjusted from a 50% cycle to an alternate cycle based on the results the operator is getting. In some embodiments, the duty cycle is set to 50%. In some embodiments, the duty cycle is set to between about 92% and about 98%. In some embodiments, the duty cycle is set to between about 2% and about 6%. The control sample is removed and the detection system 210 is rotated until the operator receives a signal (audio, visual, etc.) that the target material is detected by the detection system 210. Recording the direction to the target material from multiple positions allows for triangulation.

Figure 17:
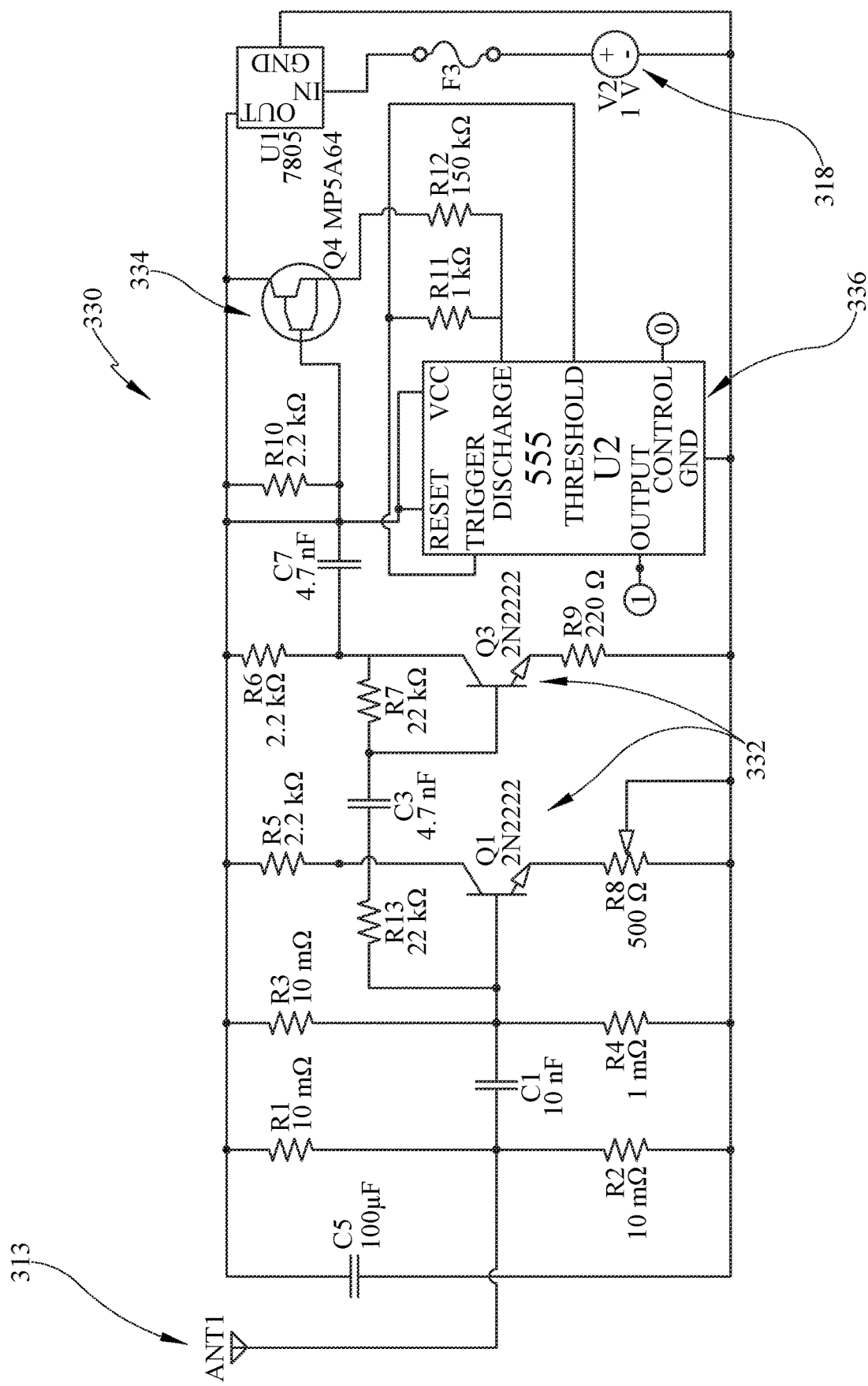
FIG. 17 is a schematic view of another exemplary embodiment of a receiver circuit according to the present disclosure.

Another exemplary embodiment of a receiver circuit 330 in accordance with the present disclosure is shown in FIG. 17. The receiver circuit 330 is similar to the circuits 30, 230. A receiver antenna 313 passes voltage through a pair of NPN 200 transistors 332. The output is capacitively coupled to a PNP Darlington transistor 334 for switching amplification. A plurality of resistors and capacitors fills in the circuit 330. The output is fed through a resistor potentiometer network to a 555 timer 336 that is used as a voltage-controlled oscillator. A received signal of given amplitude generates an audible tone at a given frequency. The output of the 555 timer 336 (at (1)) is fed to a tone generator (such as a speaker) via an audio amp. A battery 318 can be used to power the receiver circuit 330. In some embodiments, a transmitter circuit, such as circuit 220, can connect with the receiver circuit 330, such as to provide a comparative signal for use in the 555 timer 336 (at (0)) and/or speaker. In some embodiments, the circuit 330 includes a control board connected to the 555 timer 336 and/or audio amp to provide dual audio outputs for the speaker and a headset, for example.

Figure 18:
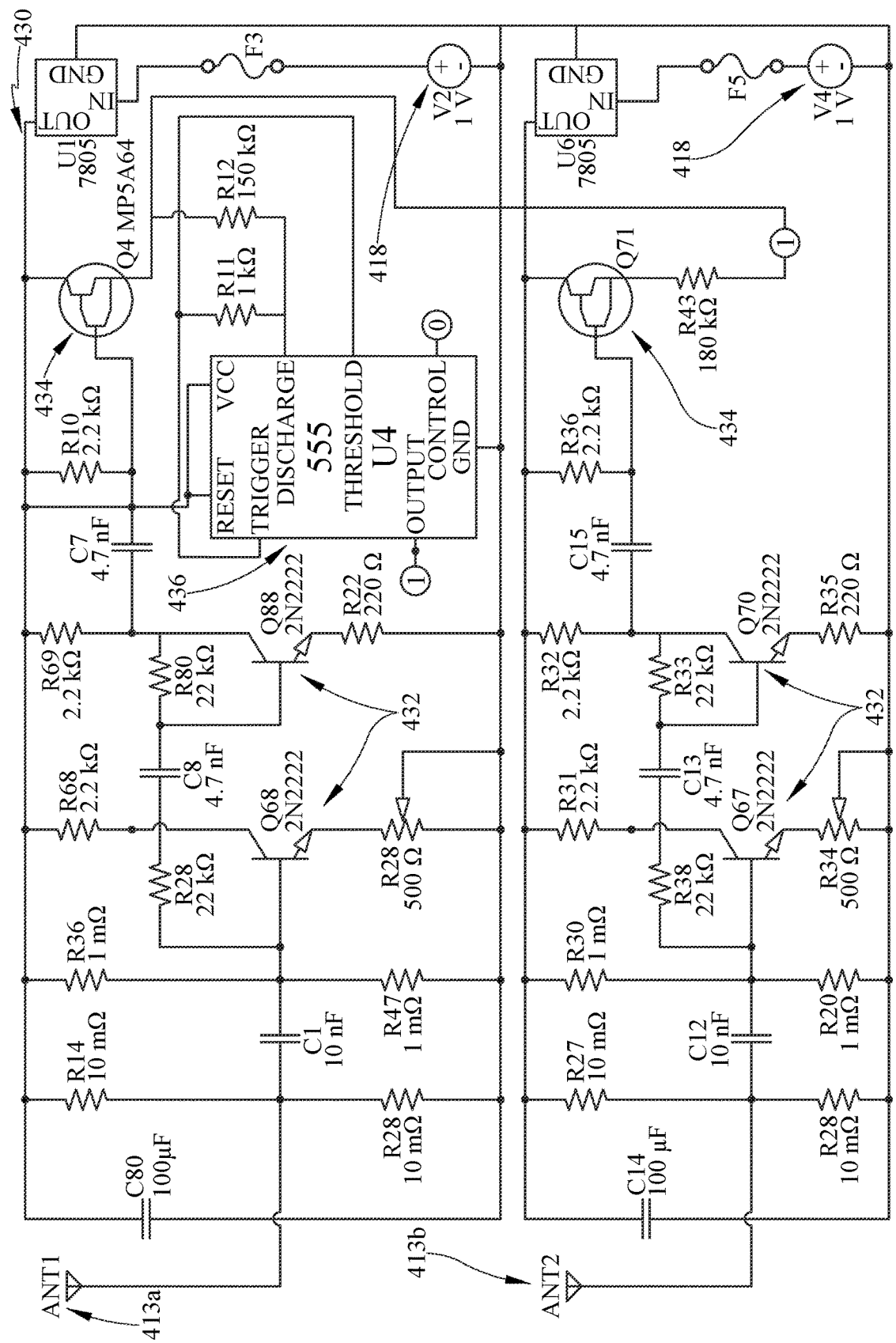
FIG. 18 is a schematic view of another exemplary embodiment of a receiver circuit according to the present disclosure.

Another exemplary embodiment of a receiver circuit 430 in accordance with the present disclosure is shown in FIG. 18. The receiver circuit 430 is similar to the circuits 30, 230, 330. Receiver antenna 413a, 413b each pass voltage through a pair of NPN 200 transistors 432. The outputs are capacitively coupled to PNP Darlington transistors 434 for switching amplification. A plurality of resistors and capacitors fills in the circuit 430. The output is fed through a resistor potentiometer network to a 555 timer 436 that is used as a voltage-controlled oscillator. A received signal of given amplitude generates an audible tone at a given frequency. The output of the 555 timer 436 (at (1)) is fed to a tone generator (such as a speaker) via an audio amp. One or more batteries 418 can be used to power the receiver circuit 430. In some embodiments, a transmitter circuit, such as circuit 220, can connect with the receiver circuit 430, such as to provide a comparative signal for use in the 555 timer 336 (at (0)) and/or speaker. In some embodiments, the circuit 430 includes a control board connected to the 555 timer 436 and/or audio amp to provide dual audio outputs for the speaker and a headset, for example.

One cannot overstate the tactical impact of a detection system according to the present disclosure capable of detecting specific explosives at ranges approaching 1 km for 1 kg of target substance. With this capability, a cache containing a few kilograms of explosive could be detected and localized from observation points not only well beyond the lethal range of the target substance, but also beyond the observation range of personnel at or near the cache. The battlefield dynamics for global counter-terror operations would be radically altered overnight. Detection systems according to the present disclosure appear to be able to detect any element or molecule but is particularly sensitive to radioactive materials which can be detected at great distances. Materials that have been placed in the ground for an extended period of time (e.g. several days) also appear more readily detectible.

In some embodiments, a detection system in accordance with the present disclosure includes a frame formed from PVC tubes having varying diameters up to about 4.75 inches, and stands on-end about 43 inches high. The detection system weighs approximately 3 pounds (lbs). The frame includes two electronics housings containing transmitter and receiver circuitry, and a 12V battery. Located near the bottom of the frame, the transmitter antenna consists of a coil wound around a one-cm PVC core. Above the transmitter antenna, and on the same axis, the receiver antenna is a short length of one-cm-diameter copper pipe. Both antennas are contained in a slotted, open-ended metal cylinder, with the slot facing in the target direction. In some embodiments, a laser or other indicator can be aligned with the opening in the directional shield to indicate the current antenna scan angle to the operator for more accurate determination of bearing angles.

One or more portions of transmitting and/or receiving circuitry may be implemented in an analog circuit configuration, a digital circuit configuration, or some combination thereof. In one example, the analog configuration may comprise one or more analog circuit components, such as, but not limited to, operational amplifiers (op-amps), resistors, inductors, and capacitors. In another example, the digital configuration may comprise one or more digital circuit components, such as, but not limited to, microprocessors, logic gates, and transistor-based switches. In some instances, a given logic gate may comprise one or more electronically controlled switches (e.g., transistors) and output of a first logic gate may control one or more logic gates disposed "downstream" from the first logic gate.

EXAMPLE

Summary of Experiment

Controlled experimentation with a detection system in accordance with the present disclosure, like those of FIGS. 1-6, on Jun. 29, 2004, Jul. 28, 2004 and Aug. 3, 2004 in Sarasota, Fla. resulted in reproducible and consistent apparent detections of diverse chemicals. Detections were made at ranges of tens to hundreds of feet for "freshly placed" samples of hydrochloric acid (30 cc, 60 cc and 120 cc) and 40 ounces of nitrocellulose double based smokeless gunpowder, and 1 to 10 miles for buried formaldehyde, a simple hydrocarbon used to disinfect and preserve human remains and found in large quantities in cemeteries.

The testing goal was to design a doubly blind (i.e., neither the operator nor the recorder knew the correct detection locations at the time of testing) test sequence to determine if the null hypothesis that the detection system randomly assigns multiple bearing angles that correspond to in place materials can be rejected with at least a 95 percent confidence level. (A 95 percent confidence level is the minimum value which meets the standard definition of statistical significance).

The null hypothesis that doubly blind formaldehyde detections to cemeteries within a 10 mile radius was a random occurrence can be rejected with a hypothetical confidence level of at least 99.93 percent" (Manifested as lines of bearings from the inventor's home and Ackerman Park where the measurements were taken). This probability is equivalent to tossing 10 heads or tails in 10 consecutive tosses of a coin. The confidence levels computed (100%–100*P) involve good approximations to the probability (P~PN,a,b,c) that a random sample of measurement values would yield "b" matches from "c" candidate values matched with "a" ground truth values with a maximum error of less than the specified maximum error of $360/(2*N)=(½)*(360/N)$.

The null hypothesis that the operator's detection of multiple samples of blindly placed hydrochloric acid was a random occurrence or guesses can be rejected with a confidence level of between 92 percent and 97 percent depending on certain assumptions as discussed herein. The detection systems in accordance with the present disclosure may have a greater probability of detection for materials that have been "in place," i.e., positioned and undisturbed, for at least several days when compared to "freshly placed" materials, i.e., materials that were positioned immediately before a test.

On Jun. 29, 2004 the recorder traveled to Sarasota, Fla. to meet the inventor and witness the operation of the detection system and administer several controlled measurement experiments. Additional testing took place on July 28th and August 3rd to assess the reproducibility and consistency of the measurements obtained by the operator on June 29th. The subsequent testing was administered by an experimental test associate at both the inventor's home and a second location approximately 10 miles to the north east of the residence.

Initial Demonstration—Smokeless Gunpowder, Jun. 29, 2004

The recorder requested that the experimental test associate procure several pounds of smokeless gunpowder. On his arrival at Tampa, Fla. on June 28th the experimental test associate informed the recorder that he obtained four 10 ounce cans of gunpowder, stored in a canvas pack and placed in the trunk of his car. The container and the smokeless gunpowder were subsequently moved to the front passenger seat of the experimental test associate's car.

Figure 11:
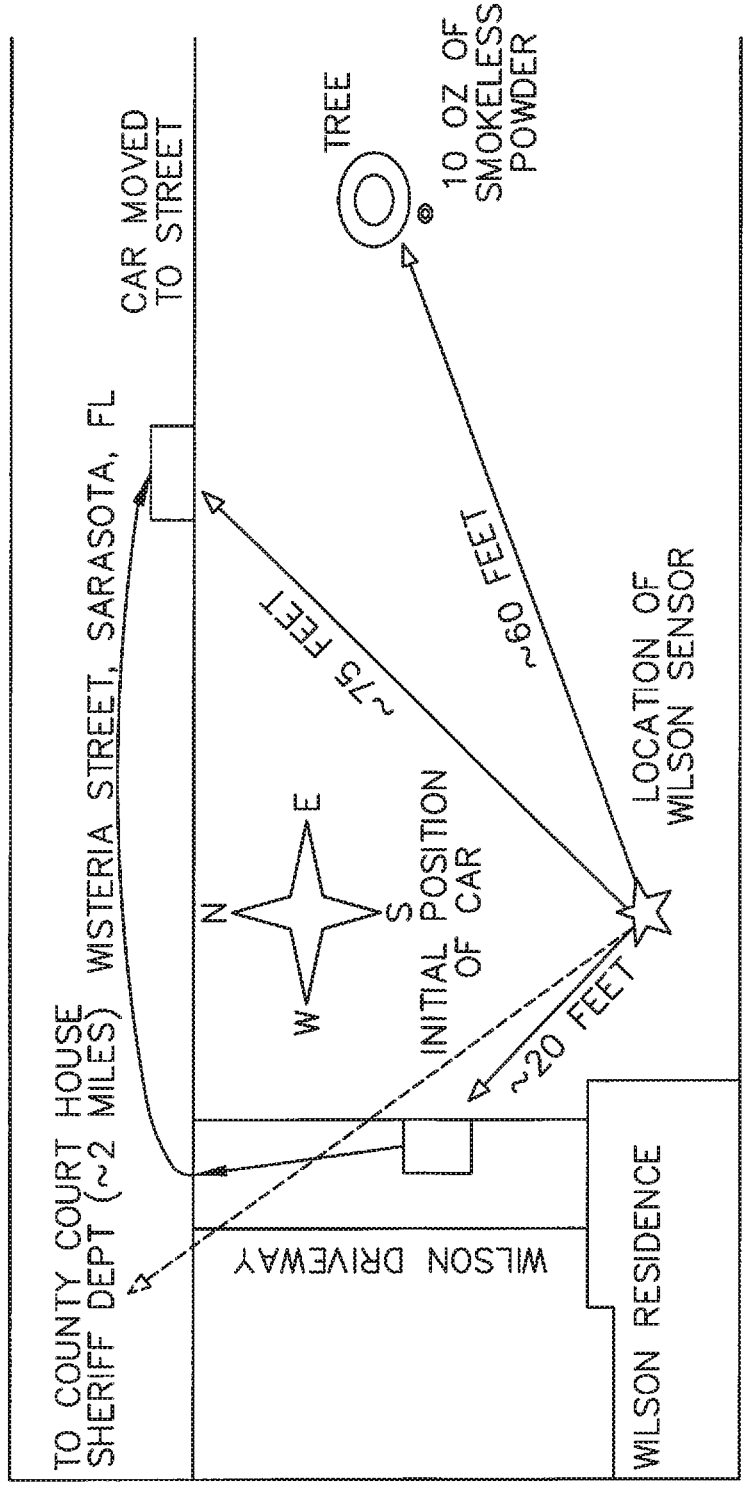
FIG. 11 is a plan view of an experimental test location.

On the morning of June 29th the recorder, the experimental test associate and the evaluator met at the inventor's home in Sarasota, Fla. at about 8:30 am. The experimental test associate parked his car in the driveway (see FIG. 11). The inventor introduced his detection system by suggesting a "witness" test for smokeless powder. Neither the inventor (acting as operator of the detection system) nor the evaluator knew of the smokeless powder contained in the experimental test associate's car. The operator positioned the detection system on his front lawn, approximately 20 feet from the door of his garage and the experimental test associate's parked car. A sample of 10 oz. of smokeless powder (inspected by the recorder and found to be unopened as evidenced by the protective factory seal) was placed by the evaluator approximately 65 feet away. The operator tuned his detection system to 1160 Hz, the frequency that corresponds to smokeless powder. The frequency was determined based on the computed frequency for nitroglycerin. However, the major constituent of smokeless powder is nitrocellulose C6H7O2(0NO2)3, which should have a tuning frequency of 152 Hz/1520 Hz or 297 Hz/2970 Hz. Certain types of smokeless gunpowder (so called "double base") powder do have small amounts of nitroglycerin added. Subsequent to the June 29th demonstration, the experimental test associate confirmed that small amounts of nitroglycerin were indeed contained in the smokeless powder used for the demonstration.

The operator identified two detections (as evidenced by a slight pitch variation in the acoustic output of his detection system). As the operator slowly rotated the detection system he identified a detection at about 315 degrees and at about 50 degrees. The 50 degree detection was clearly pointing at the sample of smokeless powder placed on the inventor's lawn. The operator attributed the 315 degree detection to ammunition stockpiled at the Sarasota Sheriff's Dept. located at about 315 degrees relative to his home and several miles away. As the 315 degree bearing detected by the operator also pointed at the front seat of the experimental test associate's car parked in the driveway the recorder quietly requested the experimental test associate move the vehicle to the street curb in front of the property, suggesting to the operator that he re-run the measurements without the experimental test associate's car potentially blocking his readings.

After the experimental test associate moved his car, the operator re-ran the gunpowder detection test. This time the operator had recorded three detections, 315, 50 and about 70 degrees, with 70 degrees pointing at the front seat of the experimental test associate's car parked on the street in front of the home. The operator's reaction at the new 70 degree detection was surprise; he wondered aloud if his detection system was operating correctly since there was not a detection at that bearing minutes before. The recorder disclosed that there was smokeless powder in the front seat of the experimental test associate's car.

Initial Test Demonstration—Analysis and Conclusions

There was no suggestion to either the operator or the evaluator that the experimental test associate had smokeless powder in his vehicle (in fact the request to obtain smokeless gun powder was not made by the recorder to the experimental test associate until the evening before his travel to Tampa). Assuming an angular uncertainty of +/−6 degrees, the chances of the operator randomly selecting a bearing angle that pointed to the gunpowder stored in the experimental test associate's car is about 3 percent or 1 in 30. Six degrees is approximately the angle subtended by a 8 foot long car at 75 feet.

In Place Material Detection Experiment—Formaldehyde

This initial test sequence was designed to be double blind and yet incorporate at least some of the detection conditions most favorable to the operator. To meet the conditions most favorable to the operator, the substance to be detected (i) had to be not freshly placed, i.e., was located at a fixed location of an extended duration, (ii) was not a commonly encountered substance that would provide multiple unrelated readings, (iii) was present in large quantities and (iv) was radioactive. The last condition could not be readily met, but the first three were satisfied by searching for formaldehyde.

In preparation for burial human remains are usually embalmed. The modern practice of embalming consists of injecting an embalming fluid into the arterial system of the deceased. Embalming fluid is prepared from a cocktail of disinfectant liquids, including a buffered solution of formaldehyde (HCHO). Formaldehyde is a colorless gas at normal conditions, and has a pungent, irritating odor. It is usually sold as a 37 percent in water, usually with 0.5 percent to 15 percent methyl alcohol added to prevent polymerization to a solid crystalline form. The molecular formula is HCHO, and the molecular weight is 30. Formaldehyde vapor is about 1.03 times as heavy as air. A 37 percent formaldehyde solution has a vapor pressure of about 1.3 mm at 68° F., and 67-88 mm at 98° F. It takes approximately three gallons of fluid to embalm a normal size body, including about one pint of formaldehyde. Cemeteries contain potential repositories of hundreds to thousands of gallons of formaldehyde solution. In the absence of air and sunlight formaldehyde is a relatively stable compound and can persist many years before chemically reacting with organic and metallic materials.

In addition to its use as a disinfectant in preserving human remains for burial, formaldehyde is a common industrial and commercial chemical. U.S. production in 1991 was 6.6 billion pounds. Major industrial uses for formaldehyde including fabrication of resins and plastics, and plywood and particle board, seed and bulb treatment, and manufacture of urea-formaldehyde insulation. However, as a suspected human carcinogenic, the American Conference of Governmental Industrial Hygienists has established a threshold limit value of 0.3 parts-per-million as a "ceiling limit," not to be exceeded at any time. While an exhaustive search was not completed, it did not appear that there were any heavy industrial users of formaldehyde in the Sarasota, Fla. area. This condition was an important consideration as searching for more commonly found materials could lead to many unverifiable detections and further ambiguity in the evaluation of the detection system.

To maintain the blind aspect of the experiment, the operator was not told what the test substance was. Instead, for each of the three tests on June 29th, the operator was given three frequencies to tune his detection system; 160 Hz, 300 Hz and 140 Hz, corresponding to the tuning frequency based on the proton number, neutron number and mass of the HCHO molecule as computed in advance by the recorder. The device was set to 350 Volts for each of the three experiments on Jun. 29, Jul. 28 and Aug. 3 2004.

The tests were doubly blind in that the recorder was not aware of the location of cemeteries in the Sarasota area until after a map of Sarasota, Fla. was purchased and studied the evening following the first day of testing. Additionally the experimental test associate, who after the initial experimental measurements on June 29th was made aware of the test substance, made no effort to locate cemeteries in the Sarasota area. This is important because no visual or other clues could have been passed between the recorder or the experimental test associate (who administered the experiments on July 28th and August 3rd) and the operator. It further must be stressed that no one other than the recorder, including the evaluator and the experimental test associate, had knowledge of the test substance before the initial set of measurements on June 29th. The operator was not informed of the location of the Youth Athletic Complex on July 28th nor the Ackerman Park location of the August 3rd experiment until just prior to departure with the experimental test associate the morning of each test. For each of the several experiments involving detection of in placed formaldehyde the appropriate tuning frequencies were only serially provided to the operator in the moments preceding the actual test, i.e., the four frequencies were not provided to the operator at the start of the testing to avoid the possibility that the operator could invert the tuning frequencies to deduce the molecule. A forth frequency, 170 Hz, was added as a control. The operator was informed by the recorder that 160 Hz and 300 Hz corresponded to one substance, and 140 Hz and 170 Hz corresponded to a second substance. In reality 160 Hz, 300 Hz and 140 Hz all equate to formaldehyde based on embodiments of methods for computing the tuning frequencies in accordance with the present disclosure.

The measured bearing angles relative to the inventor's home (June 29th and July 28th) and the Ackerman Park site (August 3rd) were measured clockwise off of North by a simple floating compass integral with the detection system, so that North is zero degrees and due East is ninety degrees. The tests were conducted on June 29th between 10:30 am and 11:30 am. Weather conditions evident during the testing were clear and hot, with temperatures in the upper 80's. Subsequent testing occurred on July 28th and August 3rd between 10 am and 12 pm with similar weather conditions. While the prevailing summer meteorological pattern in western Florida includes afternoon thunderstorms with short periods of torrential rain, several days of heavy rain preceded the August 3rd experiment.

Possible Formaldehyde Measurements: Jun. 29, 2004

The three tables of the initial June 29th measurement data are as follows. The index in the first column in the table is the order the results were written down in the field notes. The tables are sorted in increasing measured bearing angle order; the last column gives the spacing between successive measured bearing angle values in the spacing. The last entry in each table is adjacent to the first entry in each table. The first measured bearing angle spacing value gives the distance between the first and the last entry in the table.

TABLE 1

Jun. 29, 2004 Measurement Data at 160 Hz.

| Index | Measured Bearing Angle | Bearing Angle Spacing |
|---|---|---|
| 1 | 0 | 18 |
| 2 | 17 | 17 |
| 3 | 44 | 27 |
| 4 | 123 | 79 |
| 5 | 147 | 24 |
| 6 | 233 | 86 |
| 7 | 270 | 37 |
| 8 | 310 | 40 |
| 9 | 342 | 32 |

TABLE 2

Jun. 29, 2004 Measurement Data at 300 Hz.

| Index | Measured Bearing Angle | Bearing Angle Spacing |
|---|---|---|
| 2 | 17 | 23 |
| 3 | 39 | 22 |
| 4 | 58 | 19 |
| 5 | 81 | 23 |
| 6 | 98 | 17 |
| 7 | 143 | 45 |
| 8 | 167 | 24 |

TABLE 2-continued

Jun. 29, 2004 Measurement Data at 300 Hz.

| Index | Measured Bearing Angle | Bearing Angle Spacing |
|---|---|---|
| 9 | 210 | 43 |
| 10 | 222 | 12 |
| 11 | 231 | 9 |
| 12 | 267 | 36 |
| 13 | 274 | 7 |
| 14 | 292 | 18 |
| 15 | 308 | 16 |
| 16 | 325 | 17 |
| 17 | 348 | 23 |
| 1 | 354 | 6 |

TABLE 3

Jun. 29, 2004 Measurement Data at 140 Hz.

| Index | Measured Bearing Angle | Bearing Angle Spacing |
|---|---|---|
| 2 | 12 | 29 |
| 3 | 44 | 32 |
| 4 | 69 | 25 |
| 5 | 87 | 18 |
| 6 | 122 | 35 |
| 7 | 151 | 29 |
| 8 | 187 | 36 |
| 9 | 239 | 52 |
| 10 | 272 | 33 |
| 11 | 333 | 61 |
| 1 | 341 | 8 |
| 12 | 343 | 2 |

TABLE 4

Combined Measurement Data at All Three Frequencies - Jun. 29, 2004.

| Table Number | Index Number | Measured Bearing Angle | Bearing Angle Spacing |
|---|---|---|---|
| 1 | 1 | 0 | 6 |
| 3 | 2 | 12 | 12 |
| 1 | 2 | 17 | 5 |
| 2 | 2 | 17 | 0 |
| 2 | 3 | 39 | 22 |
| 1 | 3 | 44 | 5 |
| 3 | 3 | 44 | 0 |
| 2 | 4 | 58 | 14 |
| 3 | 4 | 69 | 11 |
| 2 | 5 | 81 | 12 |
| 3 | 5 | 87 | 6 |
| 2 | 6 | 98 | 11 |
| 3 | 6 | 122 | 24 |
| 1 | 4 | 123 | 1 |
| 2 | 7 | 143 | 20 |
| 1 | 5 | 147 | 4 |
| 3 | 7 | 151 | 4 |
| 2 | 8 | 167 | 16 |
| 3 | 8 | 187 | 20 |
| 2 | 9 | 210 | 23 |
| 2 | 10 | 222 | 12 |
| 2 | 11 | 231 | 9 |
| 1 | 6 | 233 | 2 |
| 3 | 9 | 239 | 6 |
| 2 | 12 | 267 | 28 |
| 1 | 7 | 270 | 3 |
| 3 | 10 | 272 | 2 |
| 2 | 13 | 274 | 2 |
| 2 | 14 | 292 | 18 |
| 2 | 15 | 308 | 16 |
| 1 | 8 | 310 | 2 |

TABLE 4-continued

Combined Measurement Data at All Three Frequencies - Jun. 29, 2004.

| Table Number | Index Number | Measured Bearing Angle | Bearing Angle Spacing |
|---|---|---|---|
| 2 | 16 | 325 | 15 |
| 3 | 11 | 333 | 8 |
| 3 | 1 | 341 | 8 |
| 1 | 9 | 342 | 1 |
| 3 | 12 | 343 | 1 |
| 2 | 17 | 348 | 5 |
| 2 | 1 | 354 | 6 |

Table 5 gives the weighted averages of the ten target angle clusters.

TABLE 5

Ground Truth Bearing Angles and Matches to Jun. 29, 2004 Data

| Index | Target Bearing Angles | Bearing Angle Spacing | Matched with Two or Three Frequency Measurements | Matched with at Least One Frequency Measurement | Distance of Dominant Target from Home (miles) |
|---|---|---|---|---|---|
| 1 | 13.00 | 21.75 | Y | Y | 9 |
| 2 | 40.00 | 27.00 | Y | Y | 2.5 |
| 3 | 63.50 | 23.50 | Y | Y | 4 |
| 4 | 78.00 | 14.50 | Y | Y | 4.1 |
| 5 | 100.75 | 22.75 | N | Y | 5 |
| 6 | 168.00 | 67.25 | N | Y | 8 |
| 7 | 210.50 | 42.50 | N | Y | 1 |
| 8 | 328.00 | 117.50 | Y | Y | 2.5 |
| 9 | 341.50 | 13.50 | Y | Y | 2.5 |
| 10 | 351.25 | 9.75 | Y | Y | 3.2 |

Candidate Target Angle Data Clustering

If two or three candidate target angles from different tables (i.e., measurements made at different frequencies) vary by less than seven degrees, they are assumed to point at the same location and their average value is used as a candidate target bearing angle for the statistical analysis that follows. If two candidate target bearing angles from the same frequency on a given day are candidates for inclusion in such a cluster, the candidate target bearing angle which is closest to the average of the candidate target bearing angles from the other frequencies are added to the cluster. At the end of this stage, each cluster contains two or three values. The process is repeated on the remaining values with a tolerance of 12 degrees rather than the initial value of seven degrees. The result of this two stage process is a set of candidate target bearing angles that are compared to known bearings to cemeteries in the Sarasota, Fla. area. This algorithm is not particularly sensitive to the choice of seven degrees in the first phase. The reason is that if a valid measurement cluster is not caught in the phase, it will probably be caught in the second phase, and vice versa. In other words, if the threshold seven degrees is decreased, then "missed" clusters will be picked up in the second phase, whereas if the seven degree threshold is increased than the additional clusters caught in the first phase would have been caught in the second phase. The main purpose of the two phases is to intelligently breakup overlapping clusters. The clustering algorithm also prevents two candidate target bearing angle values from being assigned to the same ground truth bearing angle.

Ground Truth Data Clustering

Ground truth is provided by locating all cemeteries on a map of Sarasota and measuring the bearing angles relative to the inventor's residence and the west edge of Ackerman Parks (Rand McNally Sarasota, Bradenton Florida City Map). Ground truth bearing angles are grouped into clusters with less than three degree spacing between the angles in the cluster. Occasionally in a ground truth bearing angle cluster of two or more cemeteries one cemetery was significantly closer to the inventor's residence than the others and the more distanced cemeteries were "shadowed" by the closer cemetery. Relative to the inventor's home, there are six shadow cemeteries and 10 ground truth bearing angle clusters, with 16 cemeteries in all. Relative to the Ackerman Park location there are nine ground truth bearing angle clusters.

On June 29th, three of the six triple frequency detections (i.e., detected by the operator at each of the three different frequencies related to proton number, neutron number and atomic weight) correlate with a cemetery ground truth bearing. The remaining three triple detections did not correlate to a known cemetery location. However, one of the triple detections that did not correlate to a cemetery bearing angle matched (within 7 degrees) the bearing to a nearby (1 mile) funeral home. That funeral home (Toale Brothers Funeral Home and Crematory) was surveyed and found to stockpile formaldehyde based solutions. However, detections against funeral homes were not included in the analysis, i.e., considered not valid detections for the purpose of computing the confidence level that the detection system was operating above random chance. The Sarasota, Fla. Yellow pages list 12 funeral homes in the Sarasota area, all were surveyed.

Four of the six double detections correlated with bearing angles to cemetery locations. It should be noted that one of the two double detections that did not correlate to a cemetery bearing angle did match (within 5 degrees) another nearby (1.8 mile) funeral home known to store formaldehyde based solutions. Once again, the funeral home detection was considered a miss for the computation of confidence levels. The largest ground truth bearing angle cluster contained bearing angles to three cemeteries. Each cluster was replaced by a weighted average of the values in the cluster resulting in an estimate of the 10 final ground truth bearing angles. The weights were the reciprocals of the distances of the cemeteries from the inventor's residence or the Ackerman Park location. It should also be noted that three of the multiple readings appear to correlate to funeral homes which store formaldehyde based solutions. However, detections against funeral homes were not considered valid detections for computing confidence levels of the detection system.

Matching

The ground truth bearing angle clusters were matched to the candidate target bearing angle angles if the difference was less than eight degrees in absolute value. The largest error in a match was six degrees. The closest pair of ground truth bearing angle and candidate target bearing angle that failed to be matched were separated by nineteen degrees. Therefore, if any value between 7 and 19 degrees were chosen instead of 8 degrees, there would be no change in the results for this data set.

Clustering Algorithm Results—Jun. 29, 2004

Ten ground truth bearing angles were matched to seven candidate target bearing angles corresponding to detections on at least two of the three frequencies attempted (recalling that the tuning frequencies were based on the proton number, neutron number, and atomic mass of the molecule of interest). Three cemeteries were not matched on measurement data common to at least two frequencies. These cemeteries were located at bearings of 101, 168 and 211 degrees and distances of 5, 8 and 1 miles respectively. It should be noted that detections corresponding to bearing angles to all cemeteries was made on the 300 Hz frequency, the tuning frequency computed from atomic mass of the CHOH molecule. The significance of this is currently unclear.

Five of the measured candidate target bearing angles common to two or three frequencies did not correspond to the bearing of any cemeteries. Other possible sources of formaldehyde were investigated. For example, the Sarasota Yellow Pages list 13 chemical companies or chemical distributors. These chemical suppliers were surveyed and it was determined that none of the manufacturers or distributors stockpiled any formaldehyde gas or solution. The furthest cemetery which was apparently matched was about eight miles away from the inventor's home at a bearing of about 13 degrees. But that target bearing angle was in a singleton in the candidate target bearing angle cluster and as such was not used in the computation of confidence levels. The distance from the inventor's home to the edge of the map in the Eastern direction was 6.5 miles.

Baseline Confidence Level Calculation—Jun. 29, 2004

The object of the confidence level calculation is to compute the probability that at least seven of the 12 candidate target bearing angles would match seven of the 10 ground truth bearing angles if the candidate values are randomly distributed, i.e., random guesses by the operator with no relation to physical distribution of formaldehyde and the maximum error of less than the specified maximum error of six degrees.

If the 360 degree range of candidate target bearing angles is divided into 29 bins, then each bin will have a diameter of 360/29=12.4 degrees and a radius of 6.2 degrees. The positions of the ground truth bearing angles are approximated by the center of the bins, hence if a candidate value happens to fall in the same bin as a ground truth value, it will be matched with that value.

With this standard "discretization," the problem is reduced to a classic problem in probability theory. This problem is mathematically equivalent to the question of computing the probability that a player is dealt a 12 card hand with at least seven aces from a deck of cards which contains 10 aces and 19 kings. In other words, a player is dealt 12 cards and the question is: what is the probability that the hand contains at least seven aces. The aces correspond to bins which contain a ground truth bearing angle. The kings correspond to bins which do not contain ground truth values. The deck of cards contains 29 cards in all.

Bayesian Derivation of the Probability, $P_{29,10,7,12}$

In the Bayesian approach, the positions of the card in the players hand are numbered from one to twelve corresponding to the order in which the player draws the cards from the deck. One then computes the probability that seven aces and five kings were drawn in that order. This probability is then multiplied by the number of different orderings of a hand with seven aces. The ordering of the aces and kings in a hand is determined by the position of the aces. Each position of aces corresponds to a set of seven numbers selected from the set $\{1, \ldots, 12\}$. The number of ways of ordering seven aces and five kings is given by the binomial coefficient "12 choose 7."

$$\binom{12}{7} = 792$$

To illustrate this, it is possible to consider a particular order, say AKAKAKAKAKAA where A=ace and K=king, and compute the probability that a hand with this particular order is randomly drawn. The probability that the first card is an ace is 10/29=0.34. Given that the first card was an ace (that's the Bayesian part), the probability that the second card is a king is 19/28=0.68, which is a simple consequence of Bayes formula. The probability that the third card is an ace is 9/27, that the fourth card is a king is 18/26, and so on. Each ordering has the same probability of being drawn. Therefore, the probability that seven aces were included in the hand, irrespective of the order in which the cards were drawn is $$P_{29,10,7,12} = \frac{10 \ldots 4 \cdot 19 \ldots 15}{29 \ldots 18} \binom{12}{7}$$

This problem is an example of "sampling without replacement" and is consistent with the candidate target bearing angle clustering algorithms described above.

General Formula for the Probability, $P_{N,a,b,c}$

The general formula for a deck of "N" cards with "a" aces in the deck, "b" aces in the hand, and "c" cards in the hand is $$P_{N,a,b,c} = \frac{a \ldots a-b+1 \cdot d \ldots d-e+1}{N \ldots N-c+1} \binom{c}{b}$$

where d=N−a is the number of kings in the deck and e=c−b is the number of kings in the hand.

Recasting the formula for $P_{N,a,b,c}$ back into terms of the original problem:

N=the number of bins. (N is the largest integer such that 360/N is larger than twice the maximum error).

a=the number of ground truth bearing angles.

b=the number of matches c=the number of measurements d=N−a=the number of bins with no ground truth bearing angles e=c−b=the number of false positives $P_{N,a,b,c}$=an approximation to the probability that exactly "b" matches would be found if "a" ground truth bearing angles were matched with "b" candidate target bearing angle measurements out of a total of "c" measurements where the match tolerance equals 360/N.

The Computation of $P_{29,10,7,12}$

The steps in computing $P_{29,10,7,12}$ are displayed in Table 6. The order in which the computations are performed is chosen to keep the partial products close to one. The value of P29,10,7,12=0.0269 is found in the lower right hand corner, implying there is a 2.69 percent chance of making 12 measurements of candidate bearing angles with exactly seven correct bearing angles (i.e., pointing to a known cemetery) from 29 possible measurements with ten known ground truth bearing angles and nineteen bins which to not contain ground truth values.

The first column of Table 6 provides line numbers. The second and third columns contain numbers in the numerator and denominator of the fraction to be computed. The fourth column contains the quotients of these numbers. The last column contains the cumulative products (the partial products). The "answer" is in the lower right hand corner of the table. The calculation begins with the calculation of the binomial coefficient "12 choose 7." The result, 792, is found on line 7.

TABLE 6

Computation of a 29 Bin Probability, $P_{29, 10, 7, 12}$ Jun. 29, 2004

| Line Number (i) | $X_i$ | $Y_i$ | $Z_i = X_i/Y_i$ | $Z_i \cdot Z_{i-1}$ |
|---|---|---|---|---|
| 1 | 12 | 7 | 1.714 | 1.0000 |
| 2 | 11 | 6 | 1.833 | 3.1429 |
| 3 | 10 | 5 | 2.000 | 6.2857 |
| 4 | 9 | 4 | 2.250 | 14.1429 |
| 5 | 8 | 3 | 2.667 | 37.7143 |
| 6 | 7 | 2 | 3.500 | 132.0000 |
| 7 | 6 | 1 | 6.000 | 792.0000 |
| 8 | 10 | 29 | 0.345 | 273.1034 |
| 9 | 9 | 28 | 0.321 | 87.7833 |
| 10 | 8 | 27 | 0.296 | 26.0099 |
| 11 | 7 | 26 | 0.269 | 7.0027 |
| 12 | 6 | 25 | 0.240 | 1.6806 |
| 13 | 5 | 24 | 0.208 | 0.3501 |
| 14 | 4 | 23 | 0.174 | 0.0609 |
| 15 | 19 | 22 | 0.864 | 0.0526 |
| 16 | 18 | 21 | 0.857 | 0.0451 |
| 17 | 17 | 20 | 0.850 | 0.0383 |
| 18 | 16 | 19 | 0.842 | 0.0323 |
| 19 | 15 | 18 | 0.833 | 0.0269 |

Estimation of $P_{29,10,7,12} + P_{29,10,8,12} + P_{29,10,9,12} + P_{29,10,10,12}$ Similar calculations give the probabilities for guessing the bearing angles to 8, 9, and 10 cemetery based formaldehyde deposits. Roughly, each probability is obtained by multiplying the previous by 0.2. Adding the probabilities that 7, 8, 9 or 10 bearing angles to cemeteries are randomly selected yields something less than 0.04. Hence, the final result is that the probability of the operator guessing at least seven bearings that correspond to bearing angles to cemeteries relative to his home with an accuracy of at least 6.2 degrees from 12 randomly chosen angles is slightly less than 4 percent and the corresponding confidence level for the rejection of the null hypothesis is slightly more than 96 percent. The confidence level of 96 percent means that if twenty five experiments were performed where twelve angles were randomly distributed from zero to 360 degrees then one would expect to find that seven or more of those angles would be within 6 degrees of a ground truth angle in only one of those experiments.

Jul. 28, 2004 Experiment

A critical assumption in the forgoing analysis was reproducibility. Chance events happen, but they do not occur in a reproducible fashion. On July 28th a subsequent sampling was made from the inventor's residence to test the reproducibility of the previous measurement set. The measurement experiment was administered by the experimental test associate. The operator was not aware of the test substance, or that the purpose of the test was to establish consistency between two data measurement sets. While the operator had been exposed to the frequencies of interest a month prior during the June 29th experiment, there was no indication before the test that those same frequencies would be tested. The testing began at 9:00 am with weather conditions being sunny at temperature about 80 degrees.

TABLE 7

Comparison of June 29th and Jul 28th Bearing Angle Measurements

| June 29 140 Hz | July 28 140 Hz | June 29 160 Hz | July 28 160 Hz | June 29 300 Hz | Clustered June 29 300 Hz | July 28 300 Hz | Ground Truth |
|---|---|---|---|---|---|---|---|
| 12 | 0 | 17 | 16 | 17 | 28 | 26 | 13 |
| 44 | 21 | 44 | 41 | 39 | 58 | 47 | 40 |
| 69 | 50 | 123 | 78 | 58 | 81 | 76 | 64 |
| 87 | 82 | 147 | 145 | 81 | 143 | 133 | 78 |
| 122 | 131 | 233 | 230 | 98 | 167 | 173 | 101 |
| 151 | 162 | 270 | 272 | 143 | 221 | 224 | 168 |
| 187 | 243 | 310 | 302 | 167 | 267 | 252 | 210 |
| 239 | 268 | 342 | 348 | 210 | 274 | 282 | |
| 272 | 302 | | | 222 | 300 | 300 | 328 |
| 333 | 333 | | | 231 | 336.5 | 338 | 341 |
| | | | | 267 | 354 | 358 | 351 |
| | | | | 274 | | | |
| | | | | 292 | | | |
| | | | | 308 | | | |
| | | | | 325 | | | |
| | | | | 348 | | | |
| | | | | 354 | | | |

It is immediately apparent that the June 29th and July 28th data sets are highly correlated, and with the exception of the 300 Hz data both measurement data sets have the same number of data points. A simple correlation coefficient was computed between the two sets of measurements for each frequency. The correlation coefficient between the 140 Hz measurements on June 29th and the 140 Hz measurements taken on July 28th is 0.986. The correlation coefficient between the two 160 Hz measurement sets was computed to be 0.993. The correlation coefficient for the 300 Hz data could not be directly computed because on June 28th the data set consisted of 17 data measurements, while on July 29th the measurement data set consisted of 11 measurements. However, if the target bearing clustering algorithm is employed the June 28th data set readily collapses to 11 data points. The correlation coefficient between the July 28th 300 Hz data and the clustered June 28th 300 Hz data is 0.998.

An additional experiment was run on July 28th. The analysis of the measurements taken from the inventor's home equate to a one dimensional problem; i.e., assuming the detection system is actually functioning, the target substance (i.e., formaldehyde as found in cemeteries) is along the one dimensional bearing angle indicated by the detection system. An experiment was planned for taking a series of measurements at a different location and evaluating the intersection points (if any) of the two data sets. A second experiment site was selected about 3 miles due north of the residence at the Sarasota Youth Complex. Unfortunately the geometry did not provide any geometric diversity. The data set was not analyzed.

Aug. 3, 2004 Experiment

Once it became clear that the second site data collected on July 28th did not have sufficient geometric diversity, the recorder suggested a general location north east of the inventor's residence, along I-75. The experimental test associate contacted the operator and coordinated the date and time of the next experiment, but critically did not disclose to the operator the purpose (i.e., the frequencies or target substance) or the location of the third experiment. Had the operator known the location he could potentially translate the measurements taken from his home to a new coordinate frame centered on at second test location.

The experimental test associate selected Ackerman Park, along 1-75 east of Sarasota. More specifically the site selected by the experimental test associate was located about 100 yards north of East Sawgrass Road, adjacent to a large pond. The experiment commenced at 9:40 am, weather conditions were intermittent sun and clouds with a temperature of 84 degrees.

The data measurements obtained by the operator are summarized in Table 8.

TABLE 8

Aug. 3, 2004 Experiment: Ackerman Park

| 140 Hz | 300 Hz | 160 Hz | Ground Truth wrt Ackerman Park | Error |
|---|---|---|---|---|
| 11 | 9 | | 6 | 4 |
| | | 19 | unverified | |
| | 50 | | unverified | |
| 73 | | 63 | unverified | |
| | 98 | | 94 | |
| 155 | 150 | 159 | 166 | −11 |
| 204 | 209 | 208 | 195 | 12 |
| 237 | 236 | 238 | 245 | −8 |
| | | 260 | 255 | |
| 292 | 292 | 283 | 284 | 6 |
| | | 310 | 317 | |
| 337 | | 347 | 340 | 2 |

At the time the data was analyzed, the recorder did not have a map of the area east of Sarasota, Fla. Subsequent to the calculations, it was discovered that there is a cemetery that corresponds to the 68 degree average double collected at 140 Hz and 160 Hz. This would incrementally improve the calculations.

Computation of $P_{31,9,6,7}$

A confidence level that the null hypothesis could be rejected was computed for the Ackerman Park data using the same methodology developed above for the June 29th data set. The values for a, b, c, d and e and other values are given in the following list along with the line number on which they appear in the calculation in Table 9.

$$P_{N,a,b,c} = \frac{a \ldots a-b+1 \cdot d \ldots d-e+1}{N \ldots N-c+1}\binom{c}{b}$$

1) N=the number of bins=31 (max error is 12 degrees)
2) a=the number of ground truth angles=9
3) b=the number of matches=6
4) c=the number of double or triple measurements=7
5) d=N−a=the number of bins with no ground truth=22
6) e=c−b=the number of false positives=1
7) a−b+1=4
8) d−e+1=22
9) N−c+1=25

$$P_{31,9,6,7} = \frac{9 \cdot 8 \cdot 7 \cdot 6 \cdot 5 \cdot 4 \cdot 22}{31 \cdot 30 \cdot 29 \cdot 28 \cdot 27 \cdot 26 \cdot 25} \times (7)$$

TABLE 9

| Computation of a Bin Probability, $P_{31, 9, 6, 7}$ | | | |
|---|---|---|---|
| 9 | 31 | 0.29 | 0.29 |
| 8 | 30 | 0.27 | 0.0783 |
| 7 | 29 | 0.24 | 0.0188 |
| 6 | 28 | 0.21 | 0.00394 |
| 5 | 27 | 0.185 | 0.00073 |
| 4 | 26 | 0.154 | 0.000112 |
| 22 | 25 | 0.88 | 0.000099 |

The result is P31,9,6,7=0.0007 percent with a corresponding confidence level of 99.93 percent.

Limitations of Methodology

There are four limitations of the methodology presented herein for computing confidence levels for the formaldehyde detection experiment. The assumptions made were generally conservative in that they tended to lower the computed confidence level.

The first possible limitation is that false positives in the data may actually be valid detections. The confidence level calculations only take the currently known data into account. Of the twelve candidate target bearing angles and ten ground truth bearing angles, seven were found to match. The confidence levels for the rejection of the null hypothesis were computed on that basis alone. It is quite possible that the five unmatched measurements (false positives) point to valid targets which are unknown to the experimenters. For that reason alone, it is quite likely that the true confidence values are higher than those computed here; there is no reason to believe that the ground truth data is complete. Formaldehyde is a common industrial chemical, but as a known human carcinogenic the number of facilities that could possess significant quantities is limited and possession controlled. It is widely used in the manufacture of resins and plastics, and it is not possible in the scope of this investigation to fully rule out the possibility that significant amounts are stockpiled in the greater Sarasota, Fla. area. The Sarasota, Fla. Yellow Pages were consulted for chemical manufacturers and distributors. These chemical companies were surveyed by telephone; none possessed formaldehyde. Additionally, funeral homes obviously stockpile fluids that contain formaldehyde. The bearing of funeral homes in the Sarasota, Fla. area were measured and compared to the candidate target bearing angles common to two or three frequencies. The results are summarized in Table 10.

TABLE 10

| Common Candidate Target Bearing Angles Relative to the Inventor's Home Jun. 29, 2004 and Jul. 28, 2004 | | | | | | | |
|---|---|---|---|---|---|---|---|
| 160 Hz Angles- Jul. 28, 2004 | 300 Hz Angles- Jun. 29, 2004 | 300 Hz Angles- Jul. 28, 2004 | 140 Hz Angles- Jun. 29, 2004 | 140 Hz Angles- Jul. 28, 2004 | True Cemetery Bearing Angles | Distance to Cemetery (miles) | Funeral Home Bearing Angles |
| 16 | 17 | 26 | 12 | 21 | 13 | 9 | |
| 41 | 39 | 47 | 44 | 50 | 40 | 2.5 | |
| | 58 | 76 | 69 | | 63 | 4 | 66 |

TABLE 10-continued

Common Candidate Target Bearing Angles Relative to the
Inventor's Home Jun. 29, 2004 and Jul. 28, 2004

| 160 Hz Angles-Jul. 28, 2004 | 300 Hz Angles-Jun. 29, 2004 | 300 Hz Angles-Jul. 28, 2004 | 140 Hz Angles-Jun. 29, 2004 | 140 Hz Angles-Jul. 28, 2004 | True Cemetery Bearing Angles | Distance to Cemetery (miles) | Funeral Home Bearing Angles |
|---|---|---|---|---|---|---|---|
| 78 | 81 | | 87 | 82 | 78 | 4 | |
| | 98 | | | | 101 | 5 | |
| | | 133 | 122 | 131 | | | 128 |
| 145 | 143 | | 151 | | | | 154 |
| | 167 | 173 | | 162 | 168 | 8 | 173 |
| | | | | | | | 177 |
| | | | 187 | | | | |
| | 210 | | | | 211 | 1 | |
| | 222 | 224 | | | | | |
| 230 | 231 | | 239 | 243 | | | |
| | 267 | 252 | | | | | |
| 272 | 274 | 282 | 272 | 268 | | | |
| | 292 | | | | | | |
| 302 | 308 | 300 | | 302 | | | |
| | 325 | | 333 | 333 | 328 | 2.5 | 326, 334 |
| 348 | 348 | 338 | 343 | | 342 | 2.5 | |
| | 354 | 358 | | 358 | 351 | 3.2 | 350, 351 |

A second limitation involves the use of the maximum error to drive the confidence level calculation. If the root mean square (rms) error were used to drive the calculation, then the computed confidence levels are expected to be higher. A chi-squared analysis is an example of an rms-driven calculation. The rms norm is also called the "L2 norm." A third norm is the sum of the error magnitudes (divided by the number of matches) and is called the "L-infinity norm." The L-infinity norm is the maximum of the error magnitudes. The L1, L2, and L-infinity norms are all equal in the special case when the error magnitudes are all equal. The L1 norm is the sum of the absolute values of the errors—the differences between the "candidate target values" and the "ground truth values which are matched to the candidate values"—divided by the number of the candidate values. The L-infinity norm is the maximum of the absolute values of these errors. The L2-norm is the sum of the squares of the absolute values of the errors divided by the number of the candidate values and followed by a square root. These three norms give the same number if and only if the all the errors have the same absolute value.

A L1 norm-driven computation has the intuitive appeal that the L1 norm of the error corresponds to the area on the circle covered by the matched pairs. The L2-norm has the advantage that its use is suggested by the central limit theorem—the statistics of large numbers of squares of independent errors tend to approach a chi-squared distribution.

Both the higher fidelity and the increased stability of an L1-driven or rms-driven calculation are important to the evaluation of follow-on experiments, and, its use should be considered if a follow-on experiment is planned. A Monte Carlo simulation could be performed to verify the fidelity of the computational technique. Preliminary analysis on the available data suggests that either an L1-norm driven calculation or an rms-driven calculation would likely result in higher hypothetical confidence levels.

A third limitation to the present analysis is that data values (i.e., candidate target bearing angles) that are measured in one frequency but not detected in the other two frequencies are ignored. This was done to reduce false alarms. The present clustering algorithms proceed in two stages. If a third stage was added which added all measurement values in all three tables which have not already been added to some cluster of measurement value then it is likely that the baseline confidence level would be increased. In such a scheme might be useful to weight values more highly from a table which participates in more two and three valued clusters.

A fourth limitation in this analysis is that study data was used to derive the algorithms. The use of the data, including the ground truth data, to derive the algorithms used to process the measurements from the raw data does not meet industry-standard in any sense and it limits the interpretation of these results to apply to what one would expect if the experiment were repeated. In other words, it is not possible to directly reject the null hypothesis by using "exploratory" or hypothetical confidence levels. The best one can say is that one could expect the null hypothesis to be rejected if the experiment were repeated using the algorithm derived in this experiment. This limitation is somewhat mitigated in this analysis because subsequent formaldehyde measurements and measurements involving a different substance (hydrochloric acid, HCl) at a different locations establish detection bearing accuracies that are consistent with the parameters assumed in the clustering algorithm. The hydrochloric acid detection experiment is summarized in the following section, and the hydrochloric acid confidence levels were processed using the clustering algorithms derived from the first data set to determine confidence levels of 90 percent and 92 percent.

Conclusions for Long Placed Substance Experiment

The long placed substance experiment was designed to provide data that would enable evaluation of the detection systems in accordance with the present disclosure in the best possible light. Formaldehyde is a common industrial chemical, but as a known human carcinogenic its presence in the environment is generally measured in parts per million. Preparation of human remains for burial generally requires the use of formaldehyde. Cemeteries represent significant long standing repositories of the chemical.

The detection system was tested in a doubly blind fashion to detect formaldehyde; i.e., the operator was unaware of the chemical species he was searching for—at any given time he was only provided with one of three tuning frequencies computed using his algorithms and the molecular formula of the formaldehyde molecule, and additionally with an unrelated, control frequency. Neither the operator, other site personnel, nor the evaluator were aware that the test substance was formaldehyde. Lastly, the recorder was not aware of the location of any cemeteries in the Sarasota, Fla. area until the evening following the first experiment when a map of greater Sarasota, Fla. was purchased.

The operator's detections over the three frequencies were used to compute a confidence level that the detection system was not operating in a purely random fashion. Only detections that were common to two or three of the three frequencies were used in the computation of confidence level. The measurements data from the initial experiment on June 29th was used in the derivation of clustering algorithms used to compute the confidence level. However the algorithm that was in part derived from the June 29th measurement data set was applied directly to both the July 28th measurements at the inventor's home and the August 3rd Ackerman Park data set. The computed confidence level that the null hypothesis of random chance producing that matches evidenced in the measurement data can be rejected is at least 99.93 percent.

Recently Placed Material Detection Experiment—Hydrochloric Acid—29 Jun. 2004

On the early afternoon of June 29th, the operator, the experimental test associate, the evaluator and the recorder traveled to the home of the inventor's son. The inventor's son lives on an approximately two acre lot about 10 miles from the inventor. The locations were switched to facilitate blind placement of various samples to quantify the performance of the detection system against recently placed substances.

The evening of the recorder's arrival in Florida, i.e., the evening prior to the testing described herein, the recorder visited both Home Depot and Walmart in Tampa, Fla. to obtain supplies for the experiments. The recorder purchased one gallon of 35 percent solution of hydrochloric acid and one quart of acetone at the Tampa Home Depot. The recorder also purchased several packages of identical 200 cc plastic vials from Walmart, in addition to four measuring cups (one for each substance), self-adhering shipping labels and a pint of isopropyl alcohol. The evening before the experiments the recorder placed one fluid ounce, two fluid ounces and four fluid ounces of acid in the plastic vials. The shipping labels were placed over the vials to completely cover the contents. The recorder next placed the same amounts of both tap water and alcohol in other vials. Together with several empty vials the alcohol and water filed vials were covered with shipping labels to hide the amount of the substance (the acid, water and alcohol are all colorless).

The first recently placed experiment took place at the home of the inventor's son at 1:30 pm. Weather conditions were partly cloudy and hot. The experimental test associate accompanied the operator into the house while the recorder placed the nearly one gallon of hydrochloric acid about 117 feet from the concrete driveway, at a bearing of 240 degrees off north. The gallon of acid was concealed behind a tree and was impossible to see from the home or the driveway. After the acid was placed, the operator was led out of the home and again only given a tuning number—180 Hz, which corresponds to both the number of protons and number of neutrons in the HCl molecule. The operator initially set his detection system at 320 Volts. The operator obtained detections at three bearing angles: 243, 272 and 341 degrees. The operator was now requested to lower the voltage of his emitter to 160 Volts. After adjusting the detection system and confirming the output with a volt meter, the operator positioned the detection system in the identical location (marked with chalk on the driveway) and measured 242, 271 and 341 degrees bearing. The operator was now requested to increase the frequency of his detection system an order of magnitude, to 1,800 Hz while leaving the transmitter potential at 160 Volts. After positioning the detection system the operator obtained measurements at 242, 270 and 341 degrees. Lastly, the operator was asked to increase the voltage to 320 Volts. After positioning the detection system he obtained measurements at 246 and 277 degrees. The results are shown in Table 11.

TABLE 11

Blind Test: Single Sample of Hydrochloric Acid at 117 feet, 240 Degree Bearing

| Frequency at 180 Hz Voltage at 320 V | Frequency at 180 Hz Voltage at 160 V | Frequency at 1800 Hz Voltage at 160 V | Frequency at 1800 Hz Voltage at 320 V |
| --- | --- | --- | --- |
| 242 | 243 | 242 | 246 |
| 271 | 272 | 270 | 277 |
| 341 | 341 | 341 | |

The Computation of $P_{29,1,1,3}$

The computation of $P_{29,1,1,3}$ implies:
d=28
e=2
d−e+1=27
N−c+1=27

Substituting into the general equation for P29,1,1,3 follows:

$$\left(\frac{1}{29}\right)\left(\frac{28}{28}\right)\left(\frac{27}{27}\right)\cdot\left(\frac{3}{1}\right) = \frac{3}{29} \approx \frac{1}{10} \Rightarrow 90\%$$

The value of P29,1,1,3=0.9 implying there is a 10 percent chance of making three random measurements of candidate bearing angles with exactly one correct bearing angle (i.e., pointing to a gallon of hydrochloric acid) from 29 possible measurements (i.e., 360 degrees/measurement error of 12 degrees).

Analysis and Conclusion: Single HCl Sample Experiment

The single sample blind test yields a confidence level of about 90 percent. This result is not as significant as the formaldehyde testing summarized above, but is still significantly above chance or random occurrence. The greater significance of this result however comes in the computation of an overall confidence level that the null hypothesis of random chance can be rejected. In particular, the data values used to compute 90 percent confidence levels are independent of both the formaldehyde data sets and the multiple HCl data sets summarized below. This independence means that it is possible to combine the confidence levels in a statistically meaningful way.

Multiple HCl Sample Experiment

Following the single sample of hydrochloric acid, the operator was again escorted into the house by the experimental test associate. The recorder positioned three vials containing acid at random locations over an approximately 2 acre lot. The recorder also placed an empty vial at a random location in the two acre fenced area. The recorder then requested that the operator be brought out from the home. The operator was instructed that there was one or more sample(s) of the same compound he tested for previously and that his task was to detect each and every sample and determine its bearing. The multiple sample tests experiment took place at the home of the inventor's son at about 3:00 pm. Weather conditions were partly cloudy and hot. The multiple HCl measurements are summarized in Table 12.

TABLE 12

Multiple HCl Data Sets

| Multi HCl Test 1 1800 Hz, 160 V (degrees) | Multi HCl Test 2 1800 Hz, 312 V (degrees) | Multi HCl Ground Truth Bearing Angles | Test Vial Number and Contents |
|---|---|---|---|
| 99 | 107 | | |
| | 127 | | |
| 196 | 200 | 210 | #964 -1 oz. HCl |
| | 228 | | |
| 242 | 243 | 240 | #103 - 2 oz. HCl |
| | | 250 | #668 - control - empty |
| 271 | 270 | | |
| 339 | 334 | 330 | #217 - 4 oz. HCl |

Clustering Algorithm Reviewed

The clustering algorithm derived earlier for the formaldehyde experiment clusters the measurements from two or three tables corresponding to measurements of bearing angles at three different computed frequencies. The clustering proceeds in two stages. In the first stage candidate target bearing angles measured at different frequencies are clustered together if their difference is less than 7 degrees. In the second stage, the remaining points are clustered in their difference is less than 12 degrees. The reason there are two stages is to resolve ambiguities when the measurement angles are closely spaced.

When this clustering algorithm is applied to the data analyzed herein, the result is as it would be if one merely clustered data points in different tables which differ by less than 12 degrees. This is because the data points herein are spaced sufficiently far apart.

Uncertainty Caused by Multiple Sample Sizes

Analysis of the multiple hydrochloric acid data requires another assumption regarding the minimum amount of the subject material that can be tested with the detection system. This assumption is the result of faulty experiment planning by the recorder in that each of the three vials containing hydrochloric acid had differing amounts, one fluid ounce, two fluid ounces and four fluid ounces. In hindsight, it was premature to test for sensitivity to specific amounts of the subject material. Because of the variable amounts of acid in the test vials the measurement data set has either two or three ground truth values depending on one's point of view. If one makes the assumption that the detection system could not "reliably" detect one ounce of the target substance, then there are only two ground truth values. This is referred to as the "two ounce minimum" assumption. This is the assumption that there must be at least two ounces of substance available for meaningful confidence levels to be computed.

Effect of Wider Match Tolerance

The multiple sample hydrochloric acid data sets are summarized in Table 12. Three samples of HCl that were positioned on a 2 acre lot belonging to the inventor's son; the operator was unaware of the number and position of the samples. The two data measurements—made at the same tuning frequency but at different transmitter voltage levels—apparently matched either two or three ground truth values depending on the assumption of allowable measurement tolerance. The strict application of the measurement tolerances adopted from analysis of the formaldehyde detection experiment (i.e., 8 degrees) results in two apparent detections, the 2 oz. of acid at 240 degrees apparently corresponding with the 242 degree and 243 degree readings (again corresponding to different transmitter voltage levels on the detection system) and the 4 oz. of acid at 330 degrees corresponding to measurements of 339 degrees and 334 degrees. If the matching tolerances are relaxed to 13 degrees (possible justification being that smaller samples are detected less reliably than larger samples) it is possible to match all three vials of acid. The primary effect of increasing the ground truth match tolerance to permit the third detection is that the confidence level shifts from being a real confidence level to being a hypothetical confidence level.

The two primary multiple sample HCl confidence levels computed herein are presented in Table 13. The first confidence level is real. The confidence level that is computed assuming a wider match tolerance is hypothetical.

TABLE 13

Computed Confidence Levels

| | Confidence Level |
|---|---|
| Any Amount of Substance | 92% |
| Two Ounce Minimum | 97% |

Processed Multiple HCl Sample Data

Unfortunately in addition to variable sample size another variable was introduced during test planning; namely the voltage emitted by the detection system was not fixed between the first measurement and the second measurement sequence. The voltage level of the detection system, together with the multiplier applied to the molecular criteria of the substance of interest (i.e., proton or neutron number or molecular weight), impact the detection range of the device and its ability to attenuate close in signals. On the first set of data measurements, for multiple detections, the voltage of the detection system was set to 160 Volts, the second set of measurements were made at 312 Volts, the highest voltage setting his detection system would accept at the frequency of 1800 Hz. Another problem with the test set-up was that the frequencies were 100 times multipliers to the basic tuning parameter, instead of the normal 10 times multiplier. This was done because the operator believed that higher frequencies may provide better close range accuracy (the multiple samples were spaced several hundred feet from the operator's location). An afternoon storm prevented additional testing at the more typical 180 Hz that the operator would assign to hydrochloric acid.

All five of the candidate target bearing angles in the first table match with exactly one of the seven measured candidate target bearing angles displayed in the second table (within 1.2 degrees). These five matches are included along with the ground truth angles, the ground truth matches, and the errors in the ground truth matches in Table 14. The clustering algorithm errors are the difference between the ground truth angles and the average of the Column 1 and Column 2 measured angles.

TABLE 14

Table of Measured Angle Data and Data Processing Results

| Line Number | Column 2 Measured Angle | Column 2/ Column 1 | Matching Column 1 Angle | Average Angle (avg.) | Ground Truth Match? | Ground Truth Angles | Clustering Algorithm Error |
|---|---|---|---|---|---|---|---|
| 1 | 107 | Y | 99 | 103 | N | | |
| 2 | 129 | N | | | N | | |
| 3 | 200 | Y | 196 | 198 | ?? | | |
| 4 | | | | | ?? | 210 | (12) |
| 5 | 228 | N | | | N | | |
| 6 | 243 | Y | 242 | 242.5 | Y | 240 | 2.5 |
| 7 | 270 | Y | 271 | 270.5 | N | | |
| 8 | 334 | Y | 339 | 336.5 | Y | 330 | 6.5 |

The ground truth values of 240 and 330 degrees in the above table appear to correspond to HCl quantities of 2 and 4 ounces, respectively. The error values in parenthesis on line four (4) are the difference between the 210 ground truth value and the average candidate target bearing angle (198 degrees). Since this error value is greater than the eight (8) degree ground truth matching tolerance, 210 degrees was not initially considered a matched measurement value.

Modified Ground Truth Matching Tolerance

However, it seems possible that the one ounce HCl sample at 210 degrees actually matches with the averaged measured value of 198 degrees, even though the match error (10 or 12 degrees) is larger than usual. It seems possible that if the amount of test substance falls below a certain threshold, a larger measurement error could be expected. The match of the 210 degree ground truth data to the line three measurement data would be picked up by the algorithm if the ground truth matching tolerance of 8 degrees was increased to 13 degrees. This modification to the algorithm would yield a confidence level of 97 percent in the case of the clustering algorithm which is a significant improvement over the computation of 92 percent with an 8 degree ground truth matching tolerance. The calculations of the 97 percent hypothetical confidence level that assume a 13 degree ground truth tolerance are presented below.

It is important to stress that the 97 percent confidence level with the 13 degree ground truth matching assumption is, once again, a "hypothetical confidence level" because the data used to derive them was also used to derive the 13 degree ground truth matching tolerance. More experiments are required before the appropriate ground truth matching tolerance can be determined.

Additional Observations from the Experiments

A general formula for confidence level probabilities was derived earlier. The formula is repeated here.

$$P_{N,a,b,c} = \frac{a \ldots a-b+1 \cdot d \ldots d-e+1}{N \ldots N-c+1}\binom{c}{b}$$

where N=the number of bins. (Divide 360 by twice the maximum error and either subtract one or round down to the nearest integer to obtain N.)
a=the number of ground truth angles.
b=the number of matches
c=the number of measurements
d=N−a=the number of bins with no ground truth
e=c−b=the number of false positives
$P_{N,a,b,c}$=an approximation to the probability that exactly "b" matches would be found if "a" ground truth angles were matched with "b" measurements out of a total of "c" measurements where the match tolerance equals 360/N.

The maximum error is 6.5 degrees. This means that N=27 bins are used ((1) 6.5 bin radius*2=13 degree bin width. (2) 360/13=27.69. (3) Round down to obtain N=27). The number of ground truth angles is either a=2 or a=3 depending on whether or not the "2 ounce minimum assumption" is made, respectively. For example, when the "2 ounce minimum assumption" is made, the number of ground truth angles is a=2. This array of possibilities is summarized in Table 15.

TABLE 15

Primary Probabilities Computed

| | | |
|---|---|---|
| 8 Degree Match Tolerance | No assumption on the amount of substance detection system can | $P_{27, 3, 2, 5}$ (=92 percent) |
| 8 Degree Tolerance | Assumes that the detection system can only detect 2 oz. or more of HCl | $P_{27, 3, 2, 5}$ (=97 percent) |
| Modified Matching Tolerance (set to 13 Degrees to Match 3 Data Points | Assumes detection system can detect any amount of substance | $P_{27, 3, 2, 5}$ (=97 percent) |

The resulting calculation of $P_{27,3,2,5}$ for three ground truth angles and two matches is:

$$P_{27,3,2,5} = \frac{3 \cdot 2 \cdot 24 \cdot 23 \cdot 22}{27 \cdot 26 \cdot 25 \cdot 24 \cdot 23}\binom{5}{2}$$

$$= \frac{3}{27} \cdot \frac{2}{26} \cdot \frac{22}{25} \cdot 10$$

$$= .0111 \cdot .0769 \cdot .880 \cdot 10$$

$$= .0751$$

To review the meaning of the individual numbers in the above equations, 3/27=0.0111 is the probability that the first measurement will be a "hit". 2/26=0.0769 is the probability that the second measurement will be a "hit" given that the first measurement was a hit. 22/25=0.88 is the probability that the next three measurements will be misses, given that the first two measurements were hits. Multiplying by "5 choose 2"=10 compensates for the fact that it might not be the first two measurements which were hits—it could be any two of the five measurements. Note how the "24" and "23" in the numerator cancel with the "24" and the "23" in the denominator, simplifying the probability for the misses to 22/25. This simplification occurs whenever the number of hits is one less than the number of ground truth values.

Adding in the probability that three hits were obtained (equal to about ⅕ times 0.0751) results in the probability that at least two hits were obtained brings the total up to less than 0.08 with a corresponding confidence level of 92 percent.

If it is assumed that the detection system cannot detect small quantities of HCl (i.e., eliminating the 1 oz. sample of HCl as invalid because of the size) the confidence level calculation reflects only two candidate target measurements that match two ground truth angles:

$$P_{27,2,2,5} = \frac{2 \cdot 1 \cdot 25 \cdot 24 \cdot 23}{27 \cdot 26 \cdot 25 \cdot 24 \cdot 23} \binom{5}{2}$$

$$= \frac{2}{27} \cdot \frac{1}{26} \cdot \frac{1}{1} \cdot 10$$

$$= .0741 \cdot .0385 \cdot 1 \cdot 10$$

$$= .0285$$

This corresponds to a confidence level of 97 percent.

If the ground truth matching tolerance is increased from 8 degrees to 13 degrees so that three detections are obtained, but with a maximum error of the cluster algorithm is set to 12 degrees then the number of bins is decreased to 360/24=15 bins which "rounds down" to 14. This implies the following calculation for the confidence level in this case.

$$P_{14,3,3,5} = \text{"5 choose 3"} \times 3 \times 2 \times 1 / (14 \times 13 \times 12)$$

$$= 10 \times 6 / 2184 \sim 0.027$$

This calculation yields a confidence level of about 97 percent.

In this calculation, the probability that the two non-hits in the five measurements are actually misses has been set equal to one. This is because three hits have eliminated all the ground truth values and it is certain that the other measurements will be misses. This behavior occurs whenever all the ground truth values are matched with a measured value. There are no higher degree terms to add to the probability before the confidence level is computed.

The high confidence levels computed in this analysis suggest that one can reject the possibility that the results obtained in the experiment were due to random chance. However this is not the same as the conclusion that the measurements were due to the objective performance of the detection system. To reach that conclusion it is beneficial to both postulate and prove an underlying physical mechanism and model for the effect apparently reflected in the measurement data.

In one exemplary explanation, the detection system emits a pulse into the ground at a given frequency that induces a type of resonance with concentrations of materials that resonant at the same frequency as he introduced into the ground. Every element or compound has two or three different frequencies that induce this resonance, and the frequencies are proportional to the number of protons, neutrons and the atomic or molecular weight. This resonance may be magnetic in nature.

The explanation tendered for the operation of his detection system simply does not match any apparent physical laws. Classical electromagnetism (i.e., Maxwell's Equations) does not permit a periodic signal to elicit a characteristic magnetic response from a specific material. No apparent theory in physical chemistry describes the stimulation of atoms or molecules by signals at frequencies proportional to the number or mass of atomic particles.

What is known is that low frequency signals can propagate long distances. For example, the U.S. operates an array of low frequency acoustic microphones that can detect the infrasound (i.e., fractional Hertz to tens of Hertz) signatures associated with nuclear detonations thousands of miles away. The U.S. Navy uses extremely low frequency (ELF) radio signals (40 Hz to 80 Hz) to communicate with submerged submarines because it can propagate deep underwater.

One of the difficulties posed when broadcasting in the ELF frequency range is antenna size. In order to transmit internationally using ELF frequencies, an extremely large antenna is required. The US maintains two sites, in Wisconsin and Michigan. Both sites use long power lines as antennae, in multiple strands ranging from 14 to 28 miles (22.5 to 45 kilometers) long; a sharp contrast to the detection system's 25 meters of wire tightly wound around a 1 cm diameter by 5 cm long cylinder.

There are certain thermodynamic effects that have been observed to cause low frequency oscillations in the lattice structure of materials. Any vibration of a lattice can be decomposed into a superposition of normal modes of vibration. Considering the regular lattice of atoms in a uniform solid material, one would expect there to be energy associated with the vibrations of these atoms. Because these atoms are tied together with bonds and cannot vibrate independently the vibrations take the form of collective modes which propagate through the material. Such propagating lattice vibrations are at acoustic frequencies (i.e., thousands of Hertz).

A phonon is a quantized mode of vibration occurring in a rigid crystal lattice, such as the atomic lattice of a solid. The study of phonons is an important part of solid state physics, because they contribute to many of the physical properties of materials, such as thermal and electrical conductivity. For example, the propagation of phonons is responsible for the conduction of heat in insulators, and the properties of long-wavelength phonons gives rise to sound in solids (hence the name phonon).

The confidence levels associated with the operator using the detection system in a doubly blind test on three days over a 35 day time interval suggests that neither chance nor educated guessing is likely responsible for the apparent detections.

Transmitting low frequencies associated with the Schumann resonance can "erase" evidence of prior placements of material that the detection system previously sensed. The fundamental frequency of the Schumann resonance is roughly the fundamental frequency of a spherical shell whose inside boundary is the surface of the Earth and whose outside boundary is the ionosphere, acting as a spherical shell electromagnetic waveguide cavity. More specifically, the fundamental frequency is roughly the time it takes electromagnetic radiation to go all the way around the spherical shell. Since the speed of light is about 300,000 km/sec and one cycle is the circumference of the Earth, which is about 40,000 km/cycle the fundamental frequency is about 7.5 Hz.

The Schumann Resonances are actually observed by experiment to occur at several frequencies between 6 Hz and 50 Hz; specifically 7.8, 14, 20, 26, 33, 39 and 45 Hz, with a daily variation of about +/−0.5 Hz. This daily variation has been attributed to ionospheric conditions, electromagnetic storms from the sun; and electrical storms. Since Schumann frequencies are close to the range the inventor has been investigating it is natural to speculate there could be a relationship between his detection system, the Schumann phenomena and the apparent detections of his detection system. However physics and chemistry provide no ready connection to describe the performance of his system with Schumann resonance or any other electromagnetic phenomena.

What is claimed is:

1. An apparatus for detecting the presence of a material at a distance, comprising:
   a. a transmitter circuit configured to generate electromagnetic radiation through a transmitter antenna having a frequency based on the material to be detected;
   b. a directional shield arranged around the transmitter antenna, the directional shield having an opening to provide directionality to the transmitted electromagnetic radiation; and
   c. a receiver circuit configured to generate a signal to an operator in response to the material being detected through a receiver antenna with the opening of the directional shield arranged toward the material to provide a line of bearing to the material,
   d. wherein the frequency of the transmitted electromagnetic radiation is determined based on a defining characteristic of a constituent part of the material, the defining characteristic selected from at least one of:
      i. the number of protons in the constituent part of the material;
      ii. the number of neutrons in the constituent part of the material;
      iii. the atomic mass of the constituent part of the material; and
      iv. combinations thereof.

2. The apparatus of claim 1, wherein the frequency of the transmitted electromagnetic radiation is determined based on a sum of the number of protons and atomic mass of the constituent part of the material.

3. The apparatus of claim 1, wherein the constituent part is an atom of a particular element in the periodic table.

4. The apparatus of claim 1, wherein the constituent part is a compound having a discrete atomic structure.

5. The apparatus of claim 1, wherein the frequency is equal to the defining characteristic.

6. The apparatus of claim 1, wherein the frequency is equal to the defining characteristic increased by one or more orders of magnitude.

7. The apparatus of claim 1, wherein the receiver antenna is arranged adjacent to the transmitter antenna and configured to produce a voltage into the receiver circuit for providing the signal in response to detecting the material.

8. The apparatus of claim 1, wherein the transmitter circuit includes a pulse generator, a NPN transistor, a transformer, a bridge rectifier, and a silicon controlled rectifier, wherein an output of the pulse generator is coupled to the NPN transistor, an output of the NPN transistor is coupled to the transformer, an output of the transformer is coupled to the bridge rectifier, an output of the bridge rectifier is coupled to the transmitter antenna, an output of the transmitter antenna is coupled to the silicon controlled rectifier, and an output of the silicon controlled rectifier is coupled to the bridge rectifier.

9. The apparatus of claim 8, wherein the silicon controlled rectifier is coupled to the receiver circuit.

10. The apparatus of claim 1, wherein the receiver circuit includes a NPN transistor, a PNP transistor, and a pulse generator, wherein an output of the receiver antenna is coupled to the NPN transistor, an output of the NPN transistor is coupled to the PNP transistor, an output of the PNP transistor is coupled to the pulse generator, and an output of the pulse generator is coupled to a signal generator configured to provide the signal.

11. An apparatus for detecting the presence of a material at a distance, comprising:
   a. a frame having a lower end arranged to be supported on ground and an upper end arranged to oriented substantially vertically relative to the lower end;
   b. a transmitter unit including a transmitter circuit and a transmitter antenna, the transmitter antenna positioned in the lower end of the frame, the transmitter circuit configured to generate electromagnetic radiation through the transmitter antenna having a frequency based on the material to be detected;
   c. a directional shield positioned in the lower end of the frame around the transmitter antenna, the directional shield having an opening to provide directionality to the transmitted electromagnetic radiation; and
   d. a receiver unit including a receiver circuit and a receiver antenna, the receiver antenna positioned in the lower end of the frame adjacent to the transmitter antenna, the receiver circuit configured to generate a signal to an operator in response to the material being detected through the receiver antenna with the opening of the directional shield arranged toward the material to provide a line of bearing to the material,
   e. wherein the frequency of the transmitted electromagnetic radiation is determined based on a defining characteristic of a constituent part of the material, the defining characteristic selected from at least one of:
      i. the number of protons in the constituent part of the material;
      ii. the number of neutrons in the constituent part of the material;
      iii. the atomic mass of the constituent part of the material; and
      iv. combinations thereof.

12. The apparatus of claim 11, wherein the frequency of the transmitted electromagnetic radiation is determined based on a sum of the number of protons and atomic mass of the constituent part of the material.

13. The apparatus of claim 11, wherein the constituent part is an atom of a particular element in the periodic table.

14. The apparatus of claim 11, wherein the constituent part is a compound having a discrete atomic structure.

15. The apparatus of claim 11, wherein the frequency is equal to the defining characteristic.

16. The apparatus of claim 11, wherein the frequency is equal to the defining characteristic increased by one or more orders of magnitude.

17. The apparatus of claim 11, wherein the receiver antenna is configured to produce a voltage into the receiver circuit for providing the signal in response to detecting the material.

18. The apparatus of claim 11, wherein the transmitter circuit includes a pulse generator, a NPN transistor, a transformer, a bridge rectifier, and a silicon controlled rectifier, wherein an output of the pulse generator is coupled to the NPN transistor, an output of the NPN transistor is coupled to the transformer, an output of the transformer is coupled to the bridge rectifier, an output of the bridge rectifier is coupled to the transmitter antenna, an output of the transmitter antenna is coupled to the silicon controlled rectifier, and an output of the silicon controlled rectifier is coupled to the bridge rectifier.

19. The apparatus of claim 18, wherein the silicon controlled rectifier is coupled to the receiver circuit.

20. The apparatus of claim 11, wherein the receiver circuit includes a NPN transistor, a PNP transistor, and a pulse generator, wherein an output of the receiver antenna is coupled to the NPN transistor, an output of the NPN transistor is coupled to the PNP transistor, an output of the PNP transistor is coupled to the pulse generator, and an output of the pulse generator is coupled to a signal generator configured to provide the signal.

21. A method for detecting the presence of a material at a distance, comprising:
   a. providing an apparatus, comprising
      i. a transmitter circuit configured to generate electromagnetic radiation through a transmitter antenna having a frequency based on the material to be detected;
      ii. a directional shield arranged around the transmitter antenna, the directional shield having an opening to provide directionality to the transmitted electromagnetic radiation; and
      iii. a receiver circuit;
   b. setting the frequency of the transmitted electromagnetic radiation based on a defining characteristic of a constituent part of the material, the defining characteristic selected from at least one of:
      i. the number of protons in the constituent part of the material;
      ii. the number of neutrons in the constituent part of the material;
      iii. the atomic mass of the constituent part of the material; and
      iv. combinations thereof;
   c. transmitting the electromagnetic radiation at the set frequency;
   d. detecting the material through a receiver antenna coupled to the receiver circuit in response to the opening of the directional shield being arranged toward the material to provide a line of bearing to the material; and
   e. generating a signal to an operator in response to the material being detected.

* * * * *